(12) United States Patent
Lee et al.

(10) Patent No.: US 9,290,771 B2
(45) Date of Patent: Mar. 22, 2016

(54) RECOMBINANT MICROORGANISM HAVING AN ENHANCED ABILITY TO PRODUCE PUTRESCINE AND A METHOD FOR PRODUCING PUTRESCINE USING THE SAME

(71) Applicant: CJ CHEILJEDANG CORPORATION, Seoul (KR)

(72) Inventors: Kyoung Min Lee, Seoul (KR); Seon Hye Kim, Gyeonggi-do (KR); Hye Won Um, Gyeonggi-do (KR); Min Sun Kang, Jeollanam-do (KR); Su Jin Choi, Daegu (KR); Hee Kyoung Jung, Seoul (KR); Sung Hoo Jhon, Seoul (KR); Hongxian Li, Seoul (KR); Won Sik Gwak, Gyeongsangnam-do (KR); Chong Ho Lee, Seoul (KR); Young Lyeol Yang, Gyeonggi-do (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 14/373,265

(22) PCT Filed: Jan. 21, 2013

(86) PCT No.: PCT/KR2013/000487
§ 371 (c)(1),
(2) Date: Jul. 18, 2014

(87) PCT Pub. No.: WO2013/109121
PCT Pub. Date: Jul. 25, 2013

(65) Prior Publication Data
US 2014/0363859 A1 Dec. 11, 2014

(30) Foreign Application Priority Data
Jan. 20, 2012 (KR) .................... 10-2012-0007004

(51) Int. Cl.
C12N 15/77 (2006.01)
C12N 15/52 (2006.01)
C12P 13/00 (2006.01)

(52) U.S. Cl.
CPC .............. *C12N 15/77* (2013.01); *C12N 15/52* (2013.01); *C12P 13/001* (2013.01)

(58) Field of Classification Search
None
See application file for complete search history.

(56) References Cited

U.S. PATENT DOCUMENTS

2009/0011478 A1   1/2009   Eppelmann et al.

FOREIGN PATENT DOCUMENTS

| KR | 10-2009-0107920 A | 10/2009 |
| KR | 10-2012-0064046 A | 6/2012 |
| WO | 2009/125924 A2 | 10/2009 |

OTHER PUBLICATIONS

Kind et al., "Identification and Elimination of the Competing N-Acetyldiaminopentane Pathway for Improved Production of Diaminopentane by Corynebacterium glutamicum," Appl. Environ. Microbiol. 76(15): 5175-5180, Aug. 2010.
Qian et al., "Metabolic Engineering of *Escherichia coli* for the Production of Putrescine: A Four Carbon Diamine," Biotechnology and Bioengineering 104(4): 651-662, Nov. 1, 2009.
Sakanayn et al., "Genes and enzymes of the acetyl cycle of arginine biosynthesis in Corynebacterium glutamicum: enzyme evolution in the early steps of the arginine pathway," Microbiology 142: 99-108, 1996.
Schneider and Wendisch, "Putrescine production by engineered Corynebacterium glutamicum," Appl. Microbiol. Biotechnol. 88: 859-868, 2010.
Brocker, et al., "Target genes, consensus binding site, and role of phosphorylation for the response regulator MtrA of Corynebacterium glutamicum," J. Bacteriol., 193(5):1237-49, 2011.

*Primary Examiner* — Nashaat Nashed
(74) *Attorney, Agent, or Firm* — Cooley LLP

(57) ABSTRACT

The present invention relates to a recombinant microorganism having enhanced ability to produce putrescine at high yield, wherein the activity of NCgl0101 is weakened in a microorganism of genus *Corynebacterium* that has been modified to produce putrescine, and a method for producing putrescine using the same.

9 Claims, 1 Drawing Sheet

US 9,290,771 B2

RECOMBINANT MICROORGANISM HAVING AN ENHANCED ABILITY TO PRODUCE PUTRESCINE AND A METHOD FOR PRODUCING PUTRESCINE USING THE SAME

TECHNICAL FIELD

The present invention relates to recombinant microorganisms having an enhanced ability to produce putrescine and a method for producing putrescine using the same.

BACKGROUND ART

Putrescine (or 1,4-butanediamine) is a type of polyamine, such as spermidine and spermine, and is found in gram-negative bacteria and fungi. Since putrescine is present in a wide range of concentrations in various species, it is expected to play an important role in the metabolism of microorganisms. Putrescine is commonly produced by chemical synthesis through acrylonitrile and succinonitrile from propylene. The chemical synthesis uses the substances derived from petrochemicals as starting materials and uses toxic chemicals, and thus it is not environment-friendly and has a problem of oil depletion.

In order to resolve these problems, there has been much research on developing a method for biosynthesis of putrescine by using microorganisms, that is more environment-friendly and reduces energy consumption. According to current knowledge, putrescine can be biosynthesized through two pathways. In one pathway, ornithine is produced from glutamate and the ornithine is decarboxylated to synthesize putrescine. In the other pathway, arginine is synthesized from the ornithine, agmatine is produced from the arginine, and then putrescine is synthesized from the agmatine. In addition, there are other methods for synthesizing putrescine by using a target microorganism which is transformed with the enzymes involved in the known synthetic pathways of putrescine. For example, WO09/125924 discloses a method for producing putrescine at high yield by inactivating the pathway involved in the decomposition and utilization of putrescine in *E. coli*, by inactivating the pathway in which ornithine, a precursor of putrescine, is converted to arginine, and by enhancing the biosynthetic pathway of ornithine. An article published in 2010 discloses a method for producing putrescine at high concentration by introducing and enhancing the protein that converts ornithine to putrescine into *Corynebacterium* strains which are not capable of producing putrescine. In addition it discloses a method for producing putrescine from arginine by introducing *E. coli*-derived arginine decarboxylase and agmatinase into the strains. In this regard, the ornithine pathway produced about 50 times higher amount of putrescine than the arginine pathway (Schneider et al., Appl. Microbiol. Biotechnol. 88:4, 859-868, 2010).

DISCLOSURE

Technical Problems

In this background, the present inventors identified that putrescine can be produced at high yield in a microorganism of genus *Corynebacterium* by weakening or removing the activity of NCgl0101 protein (SEQ ID NOS: 17 or 19), thereby completing the present invention.

Technical Solution

One objective of the present invention is to provide a recombinant microorganism of genus *Corynebacterium* capable of producing putrescine at high yield, which is modified to have the weakened NCgl0101 (SEQ ID NOS: 17 or 19) activity, compared to the endogenous activity thereof.

Another objective of the present invention is to provide a method for producing putrescine using the microorganism.

Advantageous Effect

When the microorganism of genus *Corynebacterium* having an improved ability to produce putrescine of the present invention is used for the production of putrecine, it is modified to weaken NCgl0101 (SEQ ID NOS: 17 or 19) activity compared to the endogenous activity thereof, and therefore, it can be produce putrescine at high yield. Accordingly, the microorganism can be widely used for the more effective production of putrescine.

BEST MODE

Figure 1:
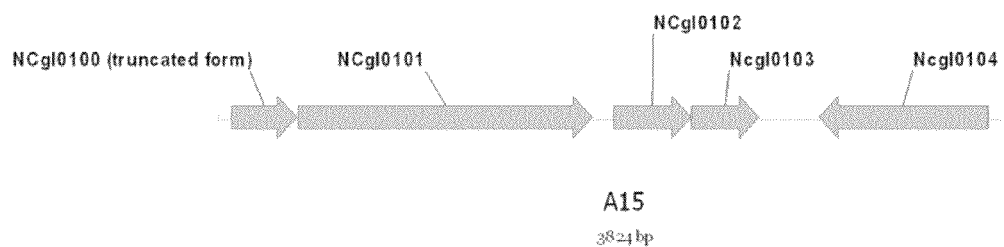
FIG. 1 represents a schematic diagram showing the relative positions of genes encoding NCgl0100 (SEQ ID NO: 27), NCgl0101 (SEQ ID NOS: 17 or 19), NCgl0102 (SEQ ID NO: 29), NCgl0103 (SEQ ID NO: 30), and NCgl0104 (SEQ ID NO: 31), which are on the chromosome of the wild type *Corynebacterium glutamicum* ATCC 13032 strain.

In one aspect to achieve the above objectives, the present invention provides a recombinant microorganism of genus *Corynebacterium* having an enhanced ability to produce putrescine, which is modified by weakening or removing the activity of NCgl0101 protein having an amino acid sequence represented by SEQ ID NO. 17 or SEQ ID NO. 19, compared to the endogenous activity thereof.

As used herein, the term "NCgl0101" means a protein showing the activity of a metal-dependent enzyme, which is expressed in *Corynebacterium glutamicum* (SEQ ID NOS: 17 or 19), and whose function is not yet fully known. It includes a metal binding domain of peptidase M20 family or aminobenzoyl-glutamate utilization protein (AbgB). The AbgB of *E. coli* constitutes aminobenzoyl-glutamate hydrolase with AbgA to hydrolyze aminobenzoyl-glutamate to aminobenzoate and glutamate. The aminobenzoate is known to be used as a precursor for folate synthesis, but its relationship with putrescine productivity has not been known.

NCgl0101 protein of the present invention may comprise the amino acid sequence represented by SEQ ID NO: 17 or SEQ ID NO: 19. However, it is not limited thereto, because there may be the difference in the amino acid sequence of the protein depending on the microbial species or strains. In other words, it can be a mutant protein or artificial variant with an amino acid sequence comprising substitution, deletion, insertion, or addition of one or several amino acids at one or more locations of the amino acid sequence represented by SEQ ID NO: 17 or SEQ ID NO: 19, as long as it can help increase the ability to produce putrescine by weakening the activity of the protein. Herein, "several" may differ depending on the location or type in the three-dimensional structure of amino acid residues of the protein, but specifically means 2 to 20, specifically 2 to 10, and more specifically 2 to 5. In addition, the substitution, deletion, insertion, addition or inversion of the amino acid includes those caused by artificial variants or natural mutation, based on the difference in the individual or species of microorganism.

The polynucleotide encoding the amino acid sequence of the present invention may comprise the polynucleotide sequence encoding the protein having amino acid sequence represented by SEQ ID NO: 17 or SEQ ID NO: 19, or the amino acid sequence of 80% or more, specifically 90% or more, more specifically 95% or more, and particularly specifically 97% or more homology with the same, as long as it has similar activity as the NCgl0101 protein. The most specifically, it may be the polynucleotide sequence represented by SEQ ID NO: 16 or SEQ ID NO: 18.

The term "homology" refers to the identity between two amino acid sequences and may be determined by the well known method to those skilled in the art, using BLAST 2.0 to compute the parameter such as score, identity and similarity.

In addition, the polynucleotide sequence encoding the polypeptide with the amino acid sequence of NCgl0101 (SEQ ID NOS: 17 or 19) of the present invention can be hybridized with the polynucleotide of SEQ ID. NO: 16 or the probe prepared from the same under 'stringent conditions', and may be a modified polynucleotide sequence encoding the NCgl0101 protein (SEQ ID NOS: 17 or 19) which normally functions. As used herein, "stringent conditions" refer to conditions which allow the specific hybridization between the polynucleotide, and are described specifically, for example, in Molecular Cloning (A Laboratory Manual, J. Sambrook et al., Editors, 2nd Edition, Cold Spring Harbor Laboratory press, Cold Spring Harbor, N. Y., 1989) or Current Protocols in Molecular Biology (F. M. Ausubel et al., Editors, John Wiley & Sons, Inc., New York). For example, the hybridization is carried out in the hybridization buffer of 65° C. (3.5× SSC, 0.02% Ficoll, 0.02% polyvinylpyrrolidone, 0.02% bovine serum albumin, 2.5 mM NaH$_2$PO$_4$ (pH 7), 0.5% SDS, 2 mM EDTA). SSC is 0.15 M sodium chloride/0.15 M sodium citrate of pH 7. After hybridization, the membrane to which DNA is transferred is rinsed with 2×SSC at room temperature and then rinsed again with 0.1 to 0.5×SSC/0.1×SDS at a temperature of 68° C.

The activity of NCgl0101 protein (SEQ ID NOS: 17 or 19) in the present invention can be weakened by 1) a partial or whole deletion of a polynucleotide encoding the protein, 2) modifying an expression regulatory sequence to reduce the expression of the polynucleotide, 3) a modification of the polynucleotide sequence on chromosome or 4) a combination thereof.

In the above, a partial or whole deletion of a polynucleotide encoding the protein can be performed by substituting the polynucleotide encoding an endogenous target protein in the chromosome to a marker gene or a polynucleotide which partial nucleotide sequence was deleted, with a vector for chromosomal gene insertion. The length of the "partial" deletion depends on the type of polynucleotide, but is specifically 2 bp to 300 bp, more specifically 2 bp to 100 bp, and further more specifically 1 bp to 5 bp.

Also, to decrease the polynucleotide expression, an expression regulatory sequence may be modified by inducing mutations in the expression regulatory sequence through deletion, insertion, conservative or non-conservative substitution of nucleotide sequence or a combination thereof to further weaken the activity of the expression regulatory sequence, or by replacing the expression regulatory sequence with the sequence having weaker activity. The expression regulatory sequence may include a sequence encoding promoter, operator sequence, ribosomal binding site and the sequence controlling the termination of transcription and translation.

In addition, the polynucleotide sequence on chromosome to weaken the activity of the protein may be modified by inducing mutations in the sequence through deletion, insertion, conservative or non-conservative substitution of nucleotide sequence or a combination thereof to further weaken the activity of the sequence, or by replacing the polynucleotide sequence with the modified sequence to have weaker activity of the protein.

Meanwhile, a microorganism of genus *Corynebacterium* having enhanced ability to produce putrescine of the present invention may be further modified to weaken the activity of ornithine carbamoyltransferase (ArgF) involved in the synthesis of arginine from ornithine and the activity of protein (NCgl1221; SEQ ID NO: 21) involved in exporting glutamate, compared to the endogenous activity thereof. In addition, the microorganism of *Corynebacterium* genus may be modified by additionally introducing the activity of ornithine decarboxylase (ODC). Also, the microorganism of genus *Corynebacterium* may be further modified to enhance the activity of acetyl glutamate synthase to convert glutamate to acetyl glutamate or ornithine acetyltransferase (ArgJ) to convert acetyl ornithine to ornithine, the activity of acetyl glutamate kinase (ArgB) to convert acetyl glutamate to acetyl glutamyl phosphate, the activity of acetyl gamma glutamyl phosphate reductase (ArgC) to convert acetyl glutamyl phosphate to acetyl glutamate semialdehyde, and the activity of acetyl ornithine amino transferase (ArgD) to convert acetyl glutamate semialdehyde to acetyl ornithine, compared to the endogenous activities thereof, thereby enhancing the biosynthetic pathway of ornithine, a putrescine precursor (Sakanyan V et al., Microbiology. 142:1, 99-108, 1996).

In this case, the ArgF, NCgl1221, ODC, ArgC, ArgJ, ArgB and ArgD may have, but are not specifically limited to, the amino acid sequences represented by SEQ ID. NO: 20, 21, 22, 23, 24, 25, 26, respectively, or the amino acid sequences with 80% or more, specifically 90% or more, more specifically 95% or more, and most specifically 97% or more homology with the same.

As used herein, the term "ornithine decarboxylase (ODC)" refers to an enzyme that produces putrescine using ornithine, and the ODC requires pyridoxalphosphate (Pyridoxal 5'-phosphate, PLP) as a coenzyme. The ODC is found in most Gram-negative bacteria and may be found in some of the intestinal bacteria such as *Lactobacillus* of Gram-positive bacteria. *E. coli* has two types of genes encoding ODC, one of which, speC, is expressed continuously at the certain concentration and the other, speF, is expressed under specific conditions (the presence of ornithine at higher than certain concentrations and low pH). Depending on species, some species, like *E. coli*, have two kinds of ODC, and others have only one type. The species such as *Escherichia* sp., *Shigella* sp., *Citrobacter* sp., *Salmonella* sp., and *Enterobacter* sp. have two kinds of ODC (speC, speF), and the strains of *Yersinia* sp., *Klebsiella* sp., *Erwinia* sp., have one kind of ODC (spec). In case of *lactobacillus*, ODC is expressed in one type of gene (speF), and is known to be induced to be expressed under the conditions of low pH or abundant ornithine and histidine.

ODC activity may be introduced to the recombinant microorganism of genus *Corynebacterium* of the present invention using genes encoding ODC derived from the various species. The polynucleotide encoding the ODC may include, but is not limited to, the polynucleotide encoding the protein consisting of the amino acid sequence represented by SEQ ID NO: 22 and the amino acid sequence of 70% or more, specifically 80% or more, more specifically 90% or more homology with the same.

In addition, the introduction of ornithine decarboxylase (ODC) activity to the microorganisms may be performed by the various methods well known in the art; for example, the method to insert the polynucleotide including a nucleotide sequence encoding ODC to chromosome, the method to introduce the polynucleotide to the microorganisms by introducing to the vector system, the method to insert the promoter which is modified or has improved activity to the upper region of nucleotide sequence encoding ODC, and the method to insert mutation to the nucleotide sequence encoding ODC. More specifically, if the nucleotide sequence encoding ODC is introduced, known CJ7 promoter may be used as a promoter to control the expression of the same.

In addition, the enhancement of the activity of ArgC, ArgJ, ArgB and ArgD can be achieved by 1) an increase of the copy number of polynucleotide encoding the enzyme, 2) a modification of the expression regulatory sequence to increase the polynucleotide expression, 3) a modification of the polynucleotide sequence encoding the enzyme on chromosome to enhance the activity of the enzyme or 4) a combination thereof.

In method 1), the increase of the copy number of polynucleotide encoding the enzyme can be achieved by operably linking the polynucleotide to the vector or by inserting the same to the chromosome of the host cell. More specifically, the copy number of polynucleotide of the host cell can be increased by introducing a vector that is capable of replicating and functioning independently, wherein the polynucleotide encoding the enzyme of the present invention is operably linked, or by introducing the vector capable of inserting the polynucleotide into the chromosome of the host cell, wherein the polynucleotide is operably linked.

As used herein, the term "vector" refers to the DNA construct comprising the nucleotide sequence of the polynucleotide encoding the target protein operably linked to the proper regulatory sequence to express the target protein in the proper host. The regulatory sequence includes the promoter which can initiate transcription, any operator sequence to control the transcription, the sequence to encode the appropriate mRNA ribosome binding site, and the sequence to control the termination of transcription and translation. The vector may be transfected into a suitable host, and then may be replicated or function independently from the host genome, and may be integrated into the genome itself.

In the present invention, any vector which is known in the art may be used without any specific limitation as long as it can be replicated in the host. Examples of commonly used vectors are plasmid, cosmid, virus and bacteriophage in natural state or recombinant state. For example, pWE15, M13, λMBL3, λMBL4, λIXII, λASHII, λAPII, λt10, λt11, Charon4A, and Charon21A can be used as a phage vector or cosmid vector, and pBR system, pUC system, pBluescriptll system, pGEM system, pTZ system, pCL system and pET system can be used as a plasmid vector. The vector which can be used in the present invention is not particularly limited and the known expression vectors can be used. Specifically, pACYC177, pACYC184, pCL, pECCG117, pUC19, pBR322, pMW118, pCC1BAC vectors can be used. Most specifically, pACYC177, pCL, pCC1BAC vectors can be used.

In addition, the vector which can insert the polynucleotide encoding the target protein into chromosome of a host cell may specifically be, for example, a shuttle vector, pECCG112 (Korean Patent Publication No. 1992-0000933) which is able to replicate by itself both in *E. coli* and *Coryneform* bacteria, but is not limited thereto.

In addition, the polynucleotide encoding the target protein in the chromosome may be replaced by a new polynucleotide by using a vector for chromosomal gene insertion. The insertion of the polynucleotide to the chromosome can be achieved by any method known in the art, for example, by homologous recombination. Since the vector of the present invention may be inserted into the chromosome by inducing a homologous recombination, the selection marker may be additionally included to confirm a successful gene insertion into the chromosome. A selection marker is for screening the cells which are transformed with the vector, in other words, for determining whether the target polynucleotide is inserted. The markers that provide selectable phenotypes such as drug resistance, auxotrophy, resistance to toxic agents or expression of surface proteins may be used. In an environment treated with a selective agent, only the cells expressing the selection marker can survive or cells show a different phenotype, and thus the successfully transformed cells can be selected through this method.

As used herein, the term "transformation" refers to the introduction of the vector comprising a polynucleotide encoding the target protein into the host cell so that the protein can be expressed in the cell. The transformed polynucleotide includes all polynucleotide which encode target proteins that can be expressed in the host cell regardless of the location, whether it is inserted into the chromosome of the host cell or located outside the chromosome. In addition, the polynucleotide includes DNA and RNA encoding the target protein. The polynucleotide may be introduced in any form as long as it can be introduced into the host cell and expressed. For example, the polynucleotide can be introduced into a host cell in a form of an expression cassette which is gene construct, comprising all the required elements for self-expression. The expression cassette typically includes a promoter operably linked to the polynucleotide, transcription termination signal, ribosomal binding site, and translation termination signal. The expression cassette may be the form of expression vector capable of self-replication. In addition, the polynucleotide may be introduced into a host cell in its own form and operably linked to the sequences required for the expression of host cell.

As used herein, the term "operably linked" refers to the functional connection between the promoter sequence initiating or mediating the transcription of polynucleotide encoding the target protein and the polynucleotide.

In addition, the method 2) modification of the expression regulatory sequence to increase the expression of the polynucleotide in the present invention may be performed by inducing the mutation of the sequence through deletion, insertion, conservative or non-conservative substitution of nucleotide sequence or a combination thereof, or by substitution by the nucleotide sequence with enhanced activity. The expression regulatory sequence includes promoter, operator sequence, sequence encoding ribosomal binding sites, and sequence to control the termination of transcription and translation.

A strong heterologous promoter may be linked to the upper of expression unit of the polynucleotide instead of original promoters. An example of a strong promoter is pcj7 promoter, lysCP1 promoter, EF-Tu promoter, groEL promoter, aceA or aceB promoter, etc., and more specifically lysCP1 promoter or pcj7 promoter derived from *Corynebacterium* is operably linked to enhance the expression of polynucleotide encoding the enzyme. Herein, lysCP1 promoter, which is an improved promoter through substitution of the nucleotide sequence of the promoter region of polynucleotide encoding aspartate kinase and aspartate semialdehyde dehydrogenase, is strong enough to increase the activity of the corresponding enzyme by 5 times compared to the wild type through enhancement of expression of aspartate kinase gene (International Patent Publication No. 2009-096689). In addition, the pcj7 promoter was identified to be expressed in *Corynebacterium ammoniagenes* and *Escherichia* and to have a strong promoter activity, and can be expressed in *Corynebacterium glutamicum* as well in high intensity (Korean Patent No. 0620092).

In addition, the method 3) modification of the polynucleotide sequence on chromosome may be performed, but are not specifically limited to, by inducing the mutation of the sequence through deletion, insertion, conservative or non-conservative substitution of nucleotide sequence or a combination thereof to enhance the activity of the sequence, or by substitution by the nucleotide sequence having enhanced activity.

The microorganism in the present invention, which is a microorganism having the ability to produce putrescine, includes prokaryotic microorganism, wherein the protein comprising amino acid sequence represented by in SEQ ID NO: 17 or SEQ ID NO: 19 is expressed, and may be, for example, the microorganism of *Escherichia* sp., *Shigella* sp., *Citrobacter* sp., *Salmonella* sp., *Enterobacter* sp., *Yersinia* sp., *Klebsiella* sp., *Erwinia* sp., *Corynebacterium* sp., *Brevibacterium* sp., *Lactobacillus* sp., *Sllenomanas* sp., and *Vibrio* sp.

The microorganism in the present invention is specifically the microorganism of genus *Corynebacterium* and may more specifically be of *Corynebacterium glutamicum*.

An embodiment of the present invention, the microorganism of genus *Corynebacterium* of accession number KCCM11138P (Korean Patent laid-open No. 2012-0064046), which has the ability to produce putrescine in a high concentration through enhanced putrescine-biosynthesis pathway, was modified. Specifically, the putrescine-producing strain KCCM11138P is the putrescine-overproducing strain, wherein the gene encoding ornithine carbamoyltransferase (ArgF) for accumulating ornithine and the gene encoding glutamate exporter (NCg11221; SEQ ID NO: 21) for increasing intracellular glutamate are deleted from ATCC13032 strains, the gene encoding ornithine decarboxylase (spec) is introduced, and the expression level of ornithine biosynthesis genes (argCJBD) is increased.

Another embodiment of the present invention, *Corynebacterium glutamicum* ATCC13869-based putrescine-producing strain DAB12-a was modified. The strain ATCC13869 was based on the same genotype as the KCCM11138P, which is putrescine-producing strain, based on *Corynebacterium glutamicum* ATCC13032. Specifically, putrescine-producing strain DAB12-a is from ATCC13869 strain obtained from American Type Culture Collection (ATCC), wherein the gene encoding ornithine carbamoyltransferase (ArgF) and the gene encoding the protein NCg11221 (SEQ ID NO: 21) to export glutamate are deleted, the gene (spec) encoding ornithine decarboxylase (ODC) derived from *E. coli* is introduced, and the promoter of ornithine biosynthesis gene operon (argCJBD) is replaced with the improved promoter.

According to one embodiment of the present invention, a microorganism of genus *Corynebacterium* (KCCM11138P) has an ability to produce putrescine, which is prepared by deletion of the gene encoding ornithine carbamoyl transferase (ArgF) and the gene encoding the glutamate exporter (NCg11221; SEQ ID NO: 21) involved in glutamate export, replacement of the own promoter of ArgCJBD gene cluster encoding an enzyme involved in the synthesis of ornithine from glutamate, and introduction of the gene (spec) encoding ornithine decarboxylase (ODC) into the chromosome in the wild-type *Corynebacterium glutamicum* ATCC13032. Based on KCCM11138P, a clone (A15) growing well in a medium containing high concentration of putrescine was selected, and it was confirmed that the selected A15 includes genes encoding NCgl0100 (SEQ ID NO: 27), NCgl0101 (SEQ ID NOS: 17 or 19), NCgl0102 (SEQ ID NO: 29), NCgl0103 (SEQ ID NO: 30) and NCgl0104 (SEQ ID NO: 31) (Example 1). In addition, the microorganism grows in the medium containing high concentration of putrescine due to the gene encoding NCgl0101 (SEQ ID NOS: 17 or 19) among the five types of genes (Example 2). As regards character of the gene encoding NCgl0101 (SEQ ID NOS: 17 or 19), it was confirmed that putrescine production was reduced in a strain in which the gene encoding NCgl0101 (SEQ ID NOS: 17 or 19) is overexpressed (Example 3), and putrescine production was increased in a strain in which the gene encoding NCgl0101 (SEQ ID NOS: 17 or 19) is deleted (Example 4).

Accordingly, the present inventors named the *Corynebacterium glutamicum* strain having an enhanced ability to produce putrescine, which is prepared by removing the NCgl0101 (SEQ ID NOS: 17 or 19) gene in the putrescine-producing strain KCCM 11138P, as *Corynebacterium glutamicum* CC01-0244, and deposited in the Korean Culture Center of Microorganisms (hereinafter, abbreviated to "KCCM") on Dec. 26, 2011, with Accession No. KCCM11241P.

In another aspect of the present invention to achieve the above objectives, the present invention relates to a method for producing putrescine, comprising the steps of:

culturing the microorganism of genus *Corynebacterium* having an enhanced ability to produce putrescine, which is modified to have the weakened activity of NCg10101 protein (SEQ ID NOS: 17 or 19) having an amino acid sequence represented by SEQ ID NO. 17 or SEQ ID NO. 19; and isolating putrescine from the culture broth obtained in the above step.

The culturing process in the present invention may be carried out in appropriate medium and under culturing conditions known in the art. Those skilled in the art can easily adjust and use the culturing process depending on selected strains. An example of the culturing process includes batch, continuous and fed-batch type cultures, but is not limited thereto. The culture medium may have to appropriately satisfy the requirements of a specific strain.

The culture medium may have to appropriately satisfy the requirements of specific strains. Culture media for various microorganisms are disclosed (for example, "Manual of Methods for General Bacteriology" from American Society for Bacteriology (Washington D.C., USA, 1981)). As a source of carbon in the medium, sugar and carbohydrates (e.g., glucose, sucrose, lactose, fructose, maltose, molasses, starch, and cellulose), butterfat and fat (e.g., soybean oil, sunflower seed oil, peanut oil and coconut oil), fatty acid (e.g., palmitic acid, stearic acid and linoleic acid), alcohol (e.g., glycerol and ethanol) and organic acid (e.g., acetic acid), etc. may be used. These substances may be used individually or as a mixture. As a source of nitrogen, nitrogen-containing organic compound (e.g., peptone, yeast extract, beef extract, malt extract, corn steep liquor, soybean meal powder and urea) or inorganic compound (e.g., ammonium sulfate, ammonium chloride, ammonium phosphate, ammonium carbonate and ammonium nitrate) may be used and these substances also may be used individually or as a mixture. As a source of phosphorus, potassium dihydrogen phosphate or dipotassium hydrogen phosphate or the corresponding sodium-containing salt may be used. In addition, the culture medium may comprise metal salt (e.g., magnesium sulfate or iron sulfate) which is essential for the growth, and finally, essential growth-promoting substances such as amino acids and vitamins, may be used in addition to the above-mentioned substances. The appropriate precursor may be added in addition to the culture medium. The feed substance may be provided in the culture at once or adequately while culturing.

The pH of the culture may be adjusted by a proper basic compound (e.g., sodium hydroxide, potassium hydroxide or ammonia) or acidic compound (e.g., phosphoric acid or sulfuric acid). Foaming may be adjusted by an anti-foaming agent such as fatty acid polyglycolester. Aerobic condition of the culture may be maintained by introducing oxygen or oxygen-containing gas mixtures, for example, air. Culturing temperature may be typically 20 to 45° C., specifically 25 to 40° C. Culturing may be continued until the production of putrescine reaches the desired maximum, it may be usually achieved in 10 to 160 hours. Putrescine may be released into culture medium, or contained in the cell.

For the method for collecting and recovering the produced putrescine in the culturing process of the present invention, the target substance may be recovered from the culture medium using the appropriate known method in the art depending on the culture method, for example, batch, continuous or fed-batch type culture.

Mode for Invention

Hereinafter, the present invention will be described in more detail with the following Examples. However, these Examples are for illustrative purposes only, and the invention is not intended to be limited by these Examples.

Example 1

Library Preparation for Selection of Effective Genes for Putrescine Biosynthesis and Selection of Clones In order to screen effective genes for putrescine biosynthesis from the chromosome of the wild-type *Corynebacterium* strain, a chromosome library of the wild-type *Corynebacterium* strain was prepared. In detail, the chromosome extracted from the wild-type *Corynebacterium glutamicum* ATCC 13032 strain was randomly cleaved with the restriction enzyme Sau3AI, and fragments of 5 to 8 kb were selected therefrom, and then cloned into an *E. coli-Corynebacterium* shuttle vector pECCG122 (Korean Patent laid-open No. 1992-0000933) to prepare a chromosome library.

In order to select effective genes for putrescine biosynthesis from the *Corynebacterium* chromosome library thus prepared, colonies growing in a medium containing high concentration of putrescine were obtained.

Meanwhile, the libraries were introduced into a microorganism of *Corynebacterium* genus (KCCM11138P) having an ability to produce putrescine, so as to prepare each of transformants. The transformants which were able to grow in a minimal medium containing 0.35 M putrescine (10 g/l of glucose, 0.4 g/l of MgSO$_4$.7H$_2$O, 4 g/l of NH$_4$Cl, 1 g/l of KH$_2$PO$_4$, 1 g/l of K$_2$HPO$_4$, 2 g/l of urea, 10 mg/l of FeSO$_4$.7H$_2$O, 1 mg/l of MnSO$_4$.5H$_2$O, 5 mg/l of nicotinamide, 5 mg/l of thiamine hydrochloride, 0.1 mg/l of biotin, 1 mM arginine, 25 mg/l of kanamycin, 0.35 M putrescine, pH 7.0) were selected. The strain KCCM11138P is disclosed in a patent applied by the present inventors (Korean Patent laid-open No. 2012-0064046), which was prepared by deleting genes encoding ornithine carbamoyltransferase (argF) and glutamate exporter (NCgl1221; SEQ ID NO: 21) in the chromosome of the wild type *Corynebacterium glutamicum* strain ATCC 13032, introducing a gene (spec) encoding ornithine decarboxylase (ODC) derived from the wild type *E. coli* W3110 strain into the chromosome, and replacing the promoter of argCJBD gene cluster encoding the enzyme involved in the synthesis of ornithine from glutamate, so as to prepare each of transformants. As a result, 275 colonies were selected, and colonies growing well in the medium containing high concentration of putrescine were secondarily identified. Each library clone was obtained and introduced into the putrescine strain again. Thereafter, colonies growing well in the medium containing high concentration of putrescine were identified and thus a clone (A15) was finally selected. This selected clone was identified by sequencing. As a result, it was confirmed that the clone comprises total 5 ORFs that encode NCgl0100 (SEQ ID NO: 27), NCgl0101 (SEQ ID NOS: 17 or 19), NCgl0102 (SEQ ID NO: 29), NCgl0103 (SEQ ID NO: 30) and NCgl0104 (SEQ ID NO: 31), of which 436 amino acids at the N-terminus were removed (FIG. 1). FIG. 1 is a schematic diagram showing the relative positions of genes encoding NCgl0100 (SEQ ID NO: 27), NCgl0101 (SEQ ID NOS: 17 or 19), NCgl0102 (SEQ ID NO: 29), NCgl0103 (SEQ ID NO: 30) and NCgl0104 (SEQ ID NO: 31), which are on the chromosome of the wild type *Corynebacterium glutamicum* ATCC 13032 strain.

Example 2

Identification of Effective Genes for Putrescine Synthesis in A15 Clone

Example 2-1

Cloning of 5 Genes in A15 Clone and Preparation of a Transformant

The nucleotide sequence of the A15 clone obtained in Example 1 was already known. Based on the nucleotide sequence of ATCC13032 strain previously reported, NCgl0100-F and NCgl0100-R represented by SEQ ID NOs. 1 and 2 as primers for amplification of the gene that encodes NCgl0100 (SEQ ID NO: 27), NCgl0100-R and tNCgl0100-F represented by SEQ ID NOs. 2 and 3 as primers for amplification of the gene that encodes tNCgl0100 (SEQ ID NO: 28) of which 436 amino acids at the N-terminus were removed, NCgl0101-F and NCgl0101-R represented by SEQ ID NOs. 4 and 5 as primers for amplification of gene that encodes NCgl0101 (SEQ ID NOS: 17 and 19), NCgl0102-F and NCgl0103-R represented by SEQ ID NOs. 6 and 7 as primers for amplification of both the genes that encode NCgl0102 (SEQ ID NO: 29) and NCgl0103 (SEQ ID NO: 30), and NCgl0104-F and NCgl0104-R represented by SEQ ID NOs. 8 and 9 as primers for amplification of the gene that encodes NCgl0104 (SEQ ID NO: 31) were constructed. In addition, P(CJ7)-F and P(CJ7)-R represented by SEQ ID NOs. 10 and 11 as primers for amplification of the expression promoter P(CJ7) (or pcj7) (Korean Patent No. 10-0620092) were constructed (Table 1).

Thereafter, PCR was carried out using the chromosome of ATCC 13032 strain as a template and each of the primer represented by SEQ ID NOs. 1 to 9 (denaturation at 95° C. for 30 seconds, annealing at 50° C. for 30 seconds, and extension at 72° C. for 1 minute~1 minute 30 seconds, 25 cycles), so as to amplify 5 types of gene fragments. In addition, PCR was carried out using the chromosome of *Corynebacterium*

*ammoniagenes* as a template and primers represented by SEQ ID NOs. 10 and 11 so as to amplify the promoter fragment.

5 genes cleaved with KpnI and XbaI, and CJ7 promoter cleaved with EcoRV and KpnI were ligated into an expression vector pHC139T (Korean Patent No. 10-0860932) cleaved with EcoRV and XbaI, so as to prepare total 5 types of expression vectors, pHC139T-P(CJ7)-NCg10100, pHC139T-P(CJ7)-tNCg10100, pHC139T-P(CJ7)-NCg10101, pHC139T-P(CJ7)-NCg10102-NCg10103, and pHC139T-P(CJ7)-NCg10104.

TABLE 1

Primers for preparation of strains expressing 5 genes contained in A15 clone

| | |
|---|---|
| NCg10100-F (SEQ ID NO. 1) | GCGCAT ATGAGCTCAAC AACCTCAAAAACC |
| NCg10100-R (SEQ ID NO. 2) | GCGTCTAGA TTATCCTT CGAGGAAGATCGCAG |
| tNCgt0100-F (SEQ ID NO. 3) | GCGCAT ATGTGGACGCT GATGGCTGC |
| NCg10101-F (SEQ ID NO. 4) | GCGCAT ATGAGTACTGA CAATTTTTCTCCAC |
| NCg10101-R (SEQ ID NO. 5) | GCGTCTAGA CTAAGCCA AATAGTCCCCTAC |
| NCg10102-F (SEQ ID NO. 6) | GCGCAT ATGGATGAACG AAGCCGGTTTG |
| NCg10103-R (SEQ ID NO. 7) | GCGTCTAGATTAATCAAT GAAGACGAATACAATTCC |
| NCg10104-F (SEQ ID NO. 8) | GCGCATATGGCGGGTGAC AAATTGTGG |
| NCg10104-R (SEQ ID NO. 9) | GCGTCTAGATTAGGACAG TTCCGCTGGAGC |
| P(CJ7)-F (SEQ ID NO. 10) | CAGATATCGCCGGCATAG CCTACCGATG |
| P(CJ7)-R (SEQ ID NO. 11) | GCGTCTAGAGATATCAGT GTTTCCTTTCG |

5 types of the expression vectors thus prepared and a control group pHC139T were introduced into the KCCM11138P strain of Example 1 by electroporation, and then spread on BHIS plates containing 25 μg/ml kanamycin to select transformants.

Example 2-2

Search of Effective Genes for Putrescine

Figure 2:
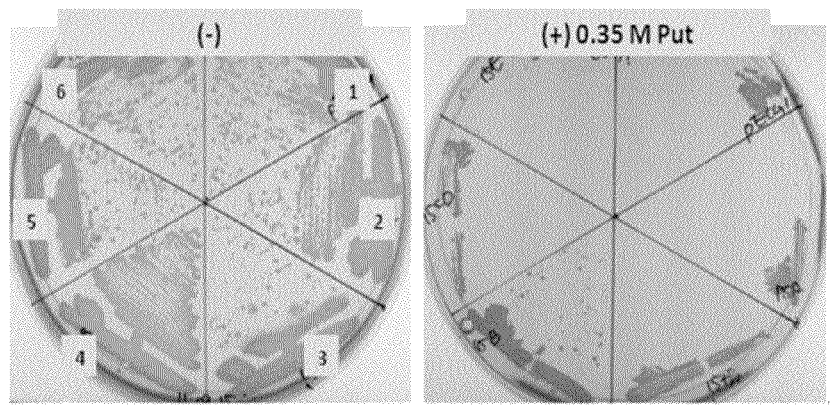
FIG. 2 represents the test result of growth comparison between the recombinant strains prepared in the present invention, in which 1, 2, 3, 4, 5 and 6 are strains prepared by introducing pHC139T, pHC139T-P(CJ7)-NCgl0100, pHC139T-P(CJ7)-tNCgl0100, pHC139T-P(CJ7)-NCgl0101, pHC139T-P(CJ7)-NCgl0102-NCgl0103, and pHC139T-P(CJ7)-NCgl0104 into KCCM11138P, respectively.

From the total 6 types of the transformants obtained in Example 2-1, transformants growing well in the medium containing high concentration of putrescine were selected in the same manner as in Example 1 (FIG. 2). FIG. 2 is the test result of comparing growth between the transformants prepared in the present invention, in which 1, 2, 3, 4, 5 and 6 represent strains introduced with the 6 types of expression vectors, pHC139T, pHC139T-P(CJ7)-NCg10100, pHC139T-P(CJ7)-tNCg10100, pHC139T-P(CJ7)-NCg10101, pHC139T-P(CJ7)-NCg10102-NCg10103 and pHC139T-P(CJ7)-NCg10104, respectively. As shown in FIG. 2, only the transformant (No. 4) introduced with pHC139T-P(CJ7)-NCg10101 showed excellent growth in the medium containing high concentration of putrescine, and thus NCg10101 (SEQ ID NOS: 17 or 19) was selected as the effective gene for putrescine biosynthesis.

Example 3

Evaluation of the Ability to Produce Putrescine in NCg10101-Overexpressing Strain The ability to produce Putrescine of the strain overexpressing the NCg10101 (SEQ ID NOS: 17 or 19) gene which was identified as the effective gene in Example 2 was evaluated. A strain for evaluation was prepared by introducing pHC139T-P(CJ7)-NCg10101 into the putrescine-producing strain KCCM11138P.

pHC139T-P(CJ7)-NCg10101 prepared in Example 2-1 and pHC139T vector as a control group were introduced into the putrescine-producing strain KCCM 11138P by electroporation, and then spread on BHIS plates containing 25 μg/ml kanamycin to select transformants. The transformants were named as KCCM 11138P/pHC139T, and KCCM 11138P/pHC139T-P(CJ7)-NCg10101, respectively. These two transformants thus selected were cultured in CM plates containing 1 mM arginine (1% glucose, 1% polypeptone, 0.5% yeast extract, 0.5% beef extract, 0.25% NaCl, 0.2% urea, 100 μl of 50% NaOH, 2% agar, pH 6.8 per 1 L) at 30° C. for 24 hours, and then a loop of cell culture was inoculated in 25 ml of titer medium of Table 2 containing 25 μg/ml kanamycin, and cultured with shaking at 200 rpm at 30° C. for 96 hours. All of the prepared strains were cultured with addition of 1 mM arginine in the medium during fermentation.

TABLE 2

| Composition | Concentration (per 1 L) |
|---|---|
| Glucose | 8% |
| Soybean protein | 0.25% |
| Corn steep solids | 0.5% |
| $(NH_4)_2SO_4$ | 4% |
| Urea | 0.15% |
| $KH_2PO_4$ | 0.1% |
| $MgSO_4 7H_2O$ | 0.05% |
| Biotin | 100 μg |
| Thiamine Hydrochloride | 3000 μg |
| Calcium-Panthotenic Acid | 3000 μg |
| Nicotinamide | 3000 μg |
| $CaCO_3$ | 5% |

As a result, as shown in Table 3, when NCg10101 (SEQ ID NOS: 17 or 19) was overexpressed, putrescine production was reduced.

TABLE 3

| Strain type | Putrescine (g/L) |
|---|---|
| KCCM 11138P/pHC139T | 9.5 |
| KCCM 11138P/pHC139T-P(CJ7) -NCg10101 | 5.1 |

Example 4

Evaluation of the Ability to Produce Putrescine in NCgl0101-Deleted Strain

Example 4-1

Preparation of NCgl0101-Deleted Strain in ATCC 13032-Based Putrescine-Producing Strain NCgl0101 (SEQ ID NOS: 17 or 19) overexpression increased cell growth in the medium containing high concentration of putrescine, but decreased putrescine production according to Example 3. On the basis of this result, the effect of NCgl0101 (SEQ ID NOS: 17 or 19) deletion on the ability to produce putrescine was examined.

In detail, based on the NCgl0101 nucleotide sequence of ATCC 13032 strain (SEQ ID NOS: 16 or 18), NCgl0101-del-F1_BamHI and NCgl0101-del-R1_SalI represented by SEQ ID NOs. 12 and 13 as primers were constructed to obtain a homologous recombinant fragment of the N-terminal region of NCgl0101 (SEQ ID NOS: 17 or 19). NCgl0101-del-F2_SalI and NCgl0101-del-R2_XbaI represented by SEQ ID NOs. 14 and 15 as primers were constructed to obtain a homologous recombinant fragment of the C-terminal region of NCgl0101 (SEQ ID NOS: 17 or 19) (Table 4). The fragments of the N-terminal and C-terminal regions of NCgl0101 gene (SEQ ID NOS: 16 or 18) were prepared by PCR using the two pairs of the primers. The PCR products were treated with BamHI & SalI and SalI & XbaI, respectively and cloned into a pDZ vector treated with BamHI & XbaI. The cloned plasmid was named as pDZ-NCgl0101(K/O).

TABLE 4

Primers for preparation of NCgl0101-deleted strains

| | |
|---|---|
| NCgl0101-del-F1_BamHI (SEQ ID NO. 12) | CGGGATCC CGGATTCCCTGCGATCATTG |
| NCgl0101-del-R1_SalI (SEQ ID NO. 13) | ACGCGTCGAC CAGTCGACGGAACTTGTGGAG |
| NCgl0101-del-F2_SalI (SEQ ID NO. 14) | ACGCGTCGAC GGCAACGACTCCGAAACCTTC |
| NCgl0101-del-R2_XbaI (SEQ ID NO. 15) | CTAGTCTAGA CTGGATCCTCATGAATGCGC |

The pDZ-NCgl0101(K/O) vector prepared for obtaining the KCCM 11138P ΔNCgl0101 strain was introduced into KCCM 11138P strain by electroporation, and then spread on the BHIS plate containing 25 μg/ml kanamycin. The successful insertion of the vector in the chromosome was confirmed by observing whether the colony was blue on the solid medium containing X-gal (5-bromo-4-chloro-3-indolyl-β-D-galactoside). The primary chromosome inserted strain was shaking-cultured in a nutrient medium (30° C., 8 hours), was then diluted from $10^{-4}$ to $10^{-10}$, and spread on the solid medium containing X-gal. While a majority of colonies appeared as blue colony, a low proportion of colonies appeared as white colonies. The NCgl0101 (SEQ ID NOS: 17 or 19) gene-deleted strains were finally selected by double crossover with the white colonies, and identified by PCR using the primers represented by SEQ ID NOs. 12 and 15. The variant thus identified was named as KCCM 11138P ΔNCgl0101.

Example 4-2

Preparation of NCgl0101-Deleted Strain in ATCC 13869-Based Putrescine-Producing Strain

*Corynebacterium glutamicum* ATCC13869-based putrescine-producing strain DAB12-a (argF-deleted, NCgl1221 (SEQ ID NOS: or 19)-deleted, *E. coli* speC-introduced, and arg operon-argCJBD promoter-substituted strain), which has the same genotype as that of the putrescine-producing strain KCCM11138P based on *Corynebacterium glutamicum* ATCC13032, was used to prepare NCgl0101 (SEQ ID NOS: 17 or 19)-deleted strains.

In detail, in order to identify the gene encoding NCgl0101 (SEQ ID NOS: 17 or 19) derived from *Corynebacterium glutamicum* ATCC13869 and the amino acid sequence of the protein expressed therefrom, PCR was carried out using the genomic DNA of *Corynebacterium glutamicum* ATCC13869 as a template and a pair of primers, SEQ ID NOs. 12 and 15 (NCgl0101-del-F1_BamHI, NCgl0101-del-R2_XbaI). Here, PCR reaction was carried out with 30 cycles of denaturation at 95° C. for 30 seconds, annealing at 53° C. for 30 seconds, and extension at 72° C. for 2 minutes and 30 seconds. The PCR products were separated by electrophoresis and their sequences were analyzed. Through sequence analysis, it was identified that the gene encoding NCgl0101 (SEQ ID NOS: 17 or 19) derived from *Corynebacterium glutamicum* ATCC13869 includes a nucleotide sequence represented by SEQ ID NO. 18 and the protein encoded thereby includes an amino acid sequence represented by SEQ ID NO. 19. When the amino acid sequences of NCgl0101 (SEQ ID NOS: 17 or 19) derived from *Corynebacterium glutamicum* ATCC13032 and that of NCgl0101 (SEQ ID NOS: 17 or 19) derived from *Corynebacterium glutamicum* ATCC13869 were compared, they showed 98% sequence homology.

In order to delete the gene encoding NCgl0101 (SEQ ID NOS: 17 or 19) derived from *Corynebacterium glutamicum* ATCC13869, the region of N-terminal and C-terminal of NCgl0101 gene (SEQ ID NOS: 16 or 18) were amplified by PCR using a genomic DNA of *Corynebacterium glutamicum* ATCC13869 as a template and two pairs of primers listed in Table 4 in the same manner as Example <4-1>. Then, the PCR products were treated with BamHI & SalI and SalI & XbaI, respectively and then cloned into the pDZ vector treated with BamHI & XbaI, thereby constructing a plasmid pDZ-2'NCgl0101(K/O).

The plasmid pDZ-2'NCgl0101(K/O) was transformed into *Corynebacterium glutamicum* DAB12-a in the same manner as in Example <4-1>, and the strain in which the gene encoding NCgl0101 (SEQ ID NOS: 17 or 19) is deleted was selected. The selected *Corynebacterium glutamicum* variant was named as DAB12-a ΔNCgl0101.

Example 4-3

Evaluation of the Ability to Produce Putrescine in NCgl0101-Deleted Strain

In order to investigate the effect of NCgl0101 (SEQ ID NOS: 17 or 19) deletion on the ability to produce putrescine in the putrescine-producing strain, the *Corynebacterium glutamicum* variants prepared in Examples <4-1> and <4-2> was compared.

In detail, the ability to putrescine in two types of *Corynebacterium glutamicum* variants (KCCM11138P ΔNCgl0101 and DAB12-a ΔNCgl0101) was evaluated in the same manner as in example 3. As shown in the following Table 5, putrescine production was found to be increased by NCgl0101 (SEQ ID NOS: 17 or 19) deletion.

TABLE 5

| Strain type | Putrescine (g/L) |
|---|---|
| KCCM 11138P | 9.8 |
| KCCM 11138P ΔNCgl0101 | 11.3 |
| DAB12-a | 10.1 |
| DAB12-a ΔNCgl0101 | 11.0 |

Taken together, the results of Examples 3 and 4 show that putrescine production was decreased by overexpression of the gene encoding NCgl0101 (SEQ ID NOS: 17 or 19) and increased by deletion of the gene in the wild type *Corynebacterium glutamicum* strain, indicating that NCgl0101 (SEQ ID NOS: 17 or 19) directly affects putrescine biosynthesis.

Accordingly, the present inventors named the *Corynebacterium glutamicum* strain having an improved ability to produce putrescine, which was prepared by deleting the NCgl0101 gene (SEQ ID NOS: 16 or 18) in the putrescine-producing strain KCCM 11138P in the above Example, as *Corynebacterium glutamicum* CC01-0244, and deposited in Korean Culture Center of Microorganisms (hereinafter, abbreviated to as "KCCM") which is international depositary authority under the Budapest Treaty on Dec. 26, 2011, with Accession No. KCCM11241P.

Based on the above descriptions, those skilled in the art will understand that the present invention may be conducted in other forms without changing the technical idea or essential technical features. In this regard, the Examples described above are to illustrate the invention in all respects, but not to limit the scope of the invention. It shall be understood that the scope of the present invention comprises any changes or modified forms derived from the meaning, scope and equivalent concept of the following claims rather than the detailed descriptions in the above.

The invention claimed is:

1. A recombinant *Corynebacterium glutamicum* having enhanced ability to produce putrescine, wherein the activity of a protein having an amino acid sequence of SEQ ID NO: 17 or SEQ ID NO: 19 is down regulated or removed, compared to the endogenous activity thereof.

2. The recombinant *Corynebacterium glutamicum* according to claim 1, wherein ornithine decarboxylase activity is introduced into the recombinant *Corynebacterium glutamicum*.

3. The recombinant *Corynebacterium glutamicum* according to claim 2, wherein the ornithine decarboxylase has the amino acid sequence of SEQ ID NO: 22.

4. The recombinant *Corynebacterium glutamicum* according to claim 1, wherein ornithine carbamoyltransferase (ArgF) activity and/or glutamate exporter activity are down regulated compared to the endogenous activity thereof.

5. The recombinant *Corynebacterium glutamicum* according to claim 4, wherein the ArgF has the amino acid sequence of SEQ ID NO: 20, and glutamate exporter has the amino acid sequence of SEQ ID NO: 21.

6. The recombinant *Corynebacterium glutamicum* according to claim 1, wherein one or more activities selected from the group consisting of acetyl gamma glutamyl phosphate reductase (ArgC) activity, acetyl glutamate synthase activity or ornithine acetyltransferase (ArgJ) activity, acetyl glutamate kinase (ArgB) activity, and acetyl ornithine amino transferase (ArgD) activity are further enhanced.

7. The recombinant *Corynebacterium glutamicum* according to claim 6, wherein ArgC, ArgJ, ArgB and ArgD have the amino acid sequences of SEQ ID NOs: 23, 24, 25, and 26, respectively.

8. The recombinant *Corynebacterium glutamicum* according to claim 1, wherein the activity of the protein is down regulated by 1) a partial or whole deletion of a polynucleotide encoding the protein, 2) a reduction of the polynucleotide expression, 3) a modification of the polynucleotide sequence on chromosome to down regulate the activity of the protein or 4) a combination thereof.

9. A method for producing putrescine, comprising culturing a recombinant *Corynebacterium glutamicum* having enhanced ability to produce putrescine in a cell culture broth, wherein the activity of a protein having an amino acid sequence of SEQ ID NO: 17 or SEQ ID NO: 19 is down regulated or removed in the recombinant *Corynebacterium glutamicum* compared to the endogenous activity thereof; obtaining the cell culture broth; and isolating putrescine from the obtained cell culture broth.

* * * * *

SEQUENCE LISTING

<160> NUMBER OF SEQ ID NOS: 31

<210> SEQ ID NO 1
<211> LENGTH: 30
<212> TYPE: DNA
<213> ORGANISM: Artificial Sequence
<220> FEATURE:
<223> OTHER INFORMATION: Primer

<400> SEQUENCE: 1
gcgcatatga gctcaacaac ctcaaaaacc                           30

<210> SEQ ID NO 2
<211> LENGTH: 32
<212> TYPE: DNA
<213> ORGANISM: Artificial Sequence
<220> FEATURE:
<223> OTHER INFORMATION: Primer

<400> SEQUENCE: 2
gcgtctagat tatccttcga ggaagatcgc ag                        32

<210> SEQ ID NO 3
<211> LENGTH: 26
<212> TYPE: DNA
<213> ORGANISM: Artificial Sequence
<220> FEATURE:
<223> OTHER INFORMATION: Primer

<400> SEQUENCE: 3
gcgcatatgt ggacgctgat ggctgc                               26

<210> SEQ ID NO 4
<211> LENGTH: 31
<212> TYPE: DNA
<213> ORGANISM: Artificial Sequence
<220> FEATURE:
<223> OTHER INFORMATION: Primer

<400> SEQUENCE: 4
gcgcatatga gtactgacaa tttttctcca c                         31

<210> SEQ ID NO 5
<211> LENGTH: 30
<212> TYPE: DNA
<213> ORGANISM: Artificial Sequence

```
<220> FEATURE:
<223> OTHER INFORMATION: Primer

<400> SEQUENCE: 5
gcgtctagac taagccaaat agtcccctac                                          30

<210> SEQ ID NO 6
<211> LENGTH: 28
<212> TYPE: DNA
<213> ORGANISM: Artificial Sequence
<220> FEATURE:
<223> OTHER INFORMATION: Primer

<400> SEQUENCE: 6
gcgcatatgg atgaacgaag ccggtttg                                            28

<210> SEQ ID NO 7
<211> LENGTH: 36
<212> TYPE: DNA
<213> ORGANISM: Artificial Sequence
<220> FEATURE:
<223> OTHER INFORMATION: Primer

<400> SEQUENCE: 7
gcgtctagat taatcaatga agacgaatac aattcc                                   36

<210> SEQ ID NO 8
<211> LENGTH: 27
<212> TYPE: DNA
<213> ORGANISM: Artificial Sequence
<220> FEATURE:
<223> OTHER INFORMATION: Primer

<400> SEQUENCE: 8
gcgcatatgg cgggtgacaa attgtgg                                             27

<210> SEQ ID NO 9
<211> LENGTH: 30
<212> TYPE: DNA
<213> ORGANISM: Artificial Sequence
<220> FEATURE:
<223> OTHER INFORMATION: Primer

<400> SEQUENCE: 9
gcgtctagat taggacagtt ccgctggagc                                          30

<210> SEQ ID NO 10
<211> LENGTH: 28
<212> TYPE: DNA
<213> ORGANISM: Artificial Sequence
<220> FEATURE:
<223> OTHER INFORMATION: Primer

<400> SEQUENCE: 10
cagatatcgc cggcatagcc taccgatg                                            28

<210> SEQ ID NO 11
<211> LENGTH: 29
<212> TYPE: DNA
<213> ORGANISM: Artificial Sequence
<220> FEATURE:
<223> OTHER INFORMATION: Primer

<400> SEQUENCE: 11
gcgtctagag atatcagtgt ttcctttcg                                           29
```

-continued

<210> SEQ ID NO 12
<211> LENGTH: 28
<212> TYPE: DNA
<213> ORGANISM: Artificial Sequence
<220> FEATURE:
<223> OTHER INFORMATION: Primer

<400> SEQUENCE: 12
cgggatcccg gattccctgc gatcattg                                      28

<210> SEQ ID NO 13
<211> LENGTH: 31
<212> TYPE: DNA
<213> ORGANISM: Artificial Sequence
<220> FEATURE:
<223> OTHER INFORMATION: Primer

<400> SEQUENCE: 13
acgcgtcgac cagtcgacgg aacttgtgga g                                  31

<210> SEQ ID NO 14
<211> LENGTH: 31
<212> TYPE: DNA
<213> ORGANISM: Artificial Sequence
<220> FEATURE:
<223> OTHER INFORMATION: Primer

<400> SEQUENCE: 14
acgcgtcgac ggcaacgact ccgaaacctt c                                  31

<210> SEQ ID NO 15
<211> LENGTH: 30
<212> TYPE: DNA
<213> ORGANISM: Artificial Sequence
<220> FEATURE:
<223> OTHER INFORMATION: Primer

<400> SEQUENCE: 15
ctagtctaga ctggatcctc atgaatgcgc                                    30

<210> SEQ ID NO 16
<211> LENGTH: 1389
<212> TYPE: DNA
<213> ORGANISM: Corynebacterium glutamicum

<400> SEQUENCE: 16
atgagtactg acaatttttc tccacaagtt ccgtcgactg tgtatttgga ttacatggag    60
caagggattg ccgcgcgcaa agcggaggca gaatctaacg ccagcacgaa gggggagagc   120
ccggattatc caggccagca ggttatttgg cgcctgatcc aggaagcagg ggagtcgttg   180
cgtgatgaac tgcgcacact ggctttcacg ctgcacgacc atccggaaga agcgttcgag   240
gaggtgttcg ccaccgagga atcacaaaaa cttctgcaaa atcatggttt tgaggttcag   300
agtggagttt atggtgttaa aaccgctcta gaaactagtt ttgaaacccc tggttatgat   360
ccagcgcagc acccaagcat tgcgatcttg gcggaatacg atgcccttcc agagatcggc   420
catgcatgcg gcacaatat catcgcagca gctggtgttg gcgcattttt agctgtcacc   480
aacatgatca aaactgccga agtgaaaggc gtggatcacc tcgactttga aggccggatc   540
gtgctgttgg aacacctgc tgaggagggg cattccggca aggaatacat gatccgaaat   600
ggcgcattcg atggcattga tgcgtcgatt atgatgcacc cctttggctt cgatctggcg   660
gagcatgttt gggtgggcag acgtaccatg acggcgacgt tccacggtgt ctctgcacac   720

```
gcgtcttcgc agcctttcat gggtaaaaat gccctcgacg ctgcaagttt ggcgtaccag    780
ggcttcggag ttttgcgtca gcaaatgcca ccgagcgacc gccttcacgc cattattacg    840
gaaggcggaa accggccaag catcattcca gacactgcaa cgatgtcgct gtacgtgcgt    900
tctttgttgc cggaagcact caaagacata tcgaaacgcg tggatgatgt gctcgatggg    960
gcggccttga tggcgggggt tggcgtcgaa aagcaatggg atgtgcaccc agctagcttg   1020
cccgtgcgca acaatcatgt gttggcgcgg cgttgggcaa aaacgcagaa tctgcgtggt   1080
cgaacggcgc tttcggaggg tattttgccc gacactctgg cagcatcgac tgattttggc   1140
aatgtctcgc acctggttcc gggcattcat ccgatggtga aaatttctcc ggaaaacgtt   1200
gcgctccaca ccaaggaatt cgccgcttat gcgcgcacgg aagaggccat cgacgcagcc   1260
gtcgacgccg caatcgggct ggcgcaagtc gccgttgacg cgcttgcaga tccgcaaatg   1320
cttatcgacg cgaccctcga gttcaccaac tccggcgacg tacttaaagt aggggactat   1380
ttggcttag                                                           1389
```

<210> SEQ ID NO 17
<211> LENGTH: 462
<212> TYPE: PRT
<213> ORGANISM: Corynebacterium glutamicum

<400> SEQUENCE: 17

```
Met Ser Thr Asp Asn Phe Ser Pro Gln Val Pro Ser Thr Val Tyr Leu
1               5                   10                  15

Asp Tyr Met Glu Gln Gly Ile Ala Ala Arg Lys Ala Glu Ala Glu Ser
            20                  25                  30

Asn Ala Ser Thr Lys Gly Glu Ser Pro Asp Tyr Pro Gly Gln Gln Val
        35                  40                  45

Ile Trp Arg Leu Ile Gln Glu Ala Gly Glu Ser Leu Arg Asp Glu Leu
    50                  55                  60

Arg Thr Leu Ala Phe Thr Leu His Asp His Pro Glu Glu Ala Phe Glu
65                  70                  75                  80

Glu Val Phe Ala Thr Glu Glu Ile Thr Lys Leu Leu Gln Asn His Gly
                85                  90                  95

Phe Glu Val Gln Ser Gly Val Tyr Gly Val Lys Thr Ala Leu Glu Thr
            100                 105                 110

Ser Phe Glu Thr Pro Gly Tyr Asp Pro Ala Gln His Pro Ser Ile Ala
        115                 120                 125

Ile Leu Ala Glu Tyr Asp Ala Leu Pro Glu Ile Gly His Ala Cys Gly
    130                 135                 140

His Asn Ile Ile Ala Ala Gly Val Gly Ala Phe Leu Ala Val Thr
145                 150                 155                 160

Asn Met Ile Lys Thr Ala Glu Val Lys Gly Val Asp His Leu Asp Phe
                165                 170                 175

Glu Gly Arg Ile Val Leu Leu Gly Thr Pro Ala Glu Glu Gly His Ser
            180                 185                 190

Gly Lys Glu Tyr Met Ile Arg Asn Gly Ala Phe Asp Gly Ile Asp Ala
        195                 200                 205

Ser Ile Met Met His Pro Phe Gly Phe Asp Leu Ala Glu His Val Trp
    210                 215                 220

Val Gly Arg Arg Thr Met Thr Ala Thr Phe His Gly Val Ser Ala His
225                 230                 235                 240

Ala Ser Ser Gln Pro Phe Met Gly Lys Asn Ala Leu Asp Ala Ala Ser
```

```
             245                 250                 255
Leu Ala Tyr Gln Gly Phe Gly Val Leu Arg Gln Gln Met Pro Pro Ser
            260                 265                 270
Asp Arg Leu His Ala Ile Ile Thr Glu Gly Gly Asn Arg Pro Ser Ile
            275                 280                 285
Ile Pro Asp Thr Ala Thr Met Ser Leu Tyr Val Arg Ser Leu Leu Pro
            290                 295                 300
Glu Ala Leu Lys Asp Ile Ser Lys Arg Val Asp Val Leu Asp Gly
305                 310                 315                 320
Ala Ala Leu Met Ala Gly Val Gly Val Glu Lys Gln Trp Asp Val His
                325                 330                 335
Pro Ala Ser Leu Pro Val Arg Asn Asn His Val Leu Ala Arg Arg Trp
            340                 345                 350
Ala Lys Thr Gln Asn Leu Arg Gly Arg Thr Ala Leu Ser Glu Gly Ile
            355                 360                 365
Leu Pro Asp Thr Leu Ala Ala Ser Thr Asp Phe Gly Asn Val Ser His
            370                 375                 380
Leu Val Pro Gly Ile His Pro Met Val Lys Ile Ser Pro Glu Asn Val
385                 390                 395                 400
Ala Leu His Thr Lys Glu Phe Ala Ala Tyr Ala Arg Thr Glu Glu Ala
                405                 410                 415
Ile Asp Ala Ala Val Asp Ala Ala Ile Gly Leu Ala Gln Val Ala Val
            420                 425                 430
Asp Ala Leu Ala Asp Pro Gln Met Leu Ile Asp Ala Thr Leu Glu Phe
            435                 440                 445
Thr Asn Ser Gly Asp Val Leu Lys Val Gly Asp Tyr Leu Ala
            450                 455                 460

<210> SEQ ID NO 18
<211> LENGTH: 1389
<212> TYPE: DNA
<213> ORGANISM: Corynebacterium glutamicum

<400> SEQUENCE: 18
atgagtactg acaatttttc tccacaagtt ccgtcgactg tgtatttgga ttacatggag      60
caagggattg tcgcgcgtaa agcggaggca gaatctaacg ccagcacgca gggggagagc     120
ccggattatc caggccagca ggttatttgg cgcctgatcc aggaagcagg ggagtcgttg     180
cgtgatgaac tgcgcacact ggctttcacg ctgcacgacc atccggaaga agcgttcgag     240
gaggtgttcg ccaccgagga aatcacaaaa cttctgcaaa tcatggtttt gaggttcag      300 agtggagttt atggtgttaa aaccgctcta gaaactagtt ttgaaacccc tggttatgat     360
ccagcgcagc acccaagcat tgcgatcttg gcggaatacg atgcccttcc agagatcggc     420
catgcgtgcg ggcacaatat catcgcagca gctggtgttg gtgcattttt ggctgtcacc     480
aacatgatca aaatgccga agtgaaaggc gtggatcacc tcgactttga aggccggatc     540
gtgctgttgg aacacctgc cgaagaaggg cattccggca aggaatacat gatccgaaat     600
ggcgcattcg atggcattga tgcatccatc atgatgcacc cctttggctt cgatctggcg     660
gaacatgttt gggtgggcag cgcactatg acggcgacgt tccacggtgt ctctgcacac     720
gcgtcttcgc agccttttcat gggtaaaaat gccctcgacg ctgcaagttt ggcgtaccag     780
ggcttcggag ttttgcgtca gcaaatgcca ccgagcgacc gccttcacgc cattattacg     840
gaaggcggaa accggccaag catcattcca gacactgcaa cgatggcgtt gtatgtgcgt     900
```

```
tccctgctgc cggaagcact caaagacata tcgaaacgcg tggatgatgt gctcgatggg    960
gcggccttga tggcgggggt tggcgtcgaa aagcaatggg atgtgcaccc agctagcttg   1020
cccgtgcgca acaatcatgt gttggcgcgg cgttgggcaa aaacgcagaa tctgcgtggt   1080
cgaacggcgc tttcggaggg catttttgccc gacactctgg cagcatcgac tgatttttggc  1140 aatgtctcgc acctgattcc gggcattcat ccgatggtga aaatttctcc ggaaaacgtt   1200
gcgctccaca ccaaggaatt cgccgcttat gcgcgcacgg aagaggccat cgacgcagcc   1260
gtcgacgccg caatcgggct ggcgcaagtc gccgttgacg cgcttgcaga tccgcaaatg   1320
cttatcgacg cgaccctcga gttcaccaac tccggcggca tgcttaaagc gggagactat   1380
ttggcttag                                                           1389
```

<210> SEQ ID NO 19
<211> LENGTH: 462
<212> TYPE: PRT
<213> ORGANISM: Corynebacterium glutamicum

<400> SEQUENCE: 19

```
Met Ser Thr Asp Asn Phe Ser Pro Gln Val Pro Ser Thr Val Tyr Leu
1               5                   10                  15

Asp Tyr Met Glu Gln Gly Ile Val Ala Arg Lys Ala Glu Ala Glu Ser
            20                  25                  30

Asn Ala Ser Thr Gln Gly Glu Ser Pro Asp Tyr Pro Gly Gln Gln Val
        35                  40                  45

Ile Trp Arg Leu Ile Gln Glu Ala Gly Glu Ser Leu Arg Asp Glu Leu
    50                  55                  60

Arg Thr Leu Ala Phe Thr Leu His Asp His Pro Glu Glu Ala Phe Glu
65                  70                  75                  80

Glu Val Phe Ala Thr Glu Glu Ile Thr Lys Leu Leu Gln Asn His Gly
                85                  90                  95

Phe Glu Val Gln Ser Gly Val Tyr Gly Val Lys Thr Ala Leu Glu Thr
            100                 105                 110

Ser Phe Glu Thr Pro Gly Tyr Asp Pro Ala Gln His Pro Ser Ile Ala
        115                 120                 125

Ile Leu Ala Glu Tyr Asp Ala Leu Pro Glu Ile Gly His Ala Cys Gly
    130                 135                 140

His Asn Ile Ile Ala Ala Gly Val Gly Ala Phe Leu Ala Val Thr
145                 150                 155                 160

Asn Met Ile Lys Asn Ala Glu Val Lys Gly Val Asp His Leu Asp Phe
                165                 170                 175

Glu Gly Arg Ile Val Leu Leu Gly Thr Pro Ala Glu Glu Gly His Ser
            180                 185                 190

Gly Lys Glu Tyr Met Ile Arg Asn Gly Ala Phe Asp Gly Ile Asp Ala
        195                 200                 205

Ser Ile Met Met His Pro Phe Gly Phe Asp Leu Ala Glu His Val Trp
    210                 215                 220

Val Gly Arg Arg Thr Met Thr Ala Thr Phe His Gly Val Ser Ala His
225                 230                 235                 240

Ala Ser Ser Gln Pro Phe Met Gly Lys Asn Ala Leu Asp Ala Ala Ser
                245                 250                 255

Leu Ala Tyr Gln Gly Phe Gly Val Leu Arg Gln Gln Met Pro Pro Ser
            260                 265                 270

Asp Arg Leu His Ala Ile Ile Thr Glu Gly Gly Asn Arg Pro Ser Ile
        275                 280                 285
```

```
Ile Pro Asp Thr Ala Thr Met Ala Leu Tyr Val Arg Ser Leu Leu Pro
    290                 295                 300

Glu Ala Leu Lys Asp Ile Ser Lys Arg Val Asp Asp Val Leu Asp Gly
305                 310                 315                 320

Ala Ala Leu Met Ala Gly Val Gly Val Glu Lys Gln Trp Asp Val His
                325                 330                 335

Pro Ala Ser Leu Pro Val Arg Asn Asn His Val Leu Ala Arg Arg Trp
                340                 345                 350

Ala Lys Thr Gln Asn Leu Arg Gly Arg Thr Ala Leu Ser Glu Gly Ile
                355                 360                 365

Leu Pro Asp Thr Leu Ala Ala Ser Thr Asp Phe Gly Asn Val Ser His
370                 375                 380

Leu Ile Pro Gly Ile His Pro Met Val Lys Ile Ser Pro Glu Asn Val
385                 390                 395                 400

Ala Leu His Thr Lys Glu Phe Ala Ala Tyr Ala Arg Thr Glu Glu Ala
                405                 410                 415

Ile Asp Ala Ala Val Asp Ala Ala Ile Gly Leu Ala Gln Val Ala Val
                420                 425                 430

Asp Ala Leu Ala Asp Pro Gln Met Leu Ile Asp Ala Thr Leu Glu Phe
                435                 440                 445

Thr Asn Ser Gly Gly Met Leu Lys Ala Gly Asp Tyr Leu Ala
450                 455                 460

<210> SEQ ID NO 20
<211> LENGTH: 319
<212> TYPE: PRT
<213> ORGANISM: Corynebacterium glutamicum

<400> SEQUENCE: 20

Met Thr Ser Gln Pro Gln Val Arg His Phe Leu Ala Asp Asp Asp Leu
1               5                   10                  15

Thr Pro Ala Glu Gln Ala Glu Val Leu Thr Leu Ala Ala Lys Leu Lys
                20                  25                  30

Ala Ala Pro Phe Ser Glu Arg Pro Leu Glu Gly Pro Lys Ser Val Ala
                35                  40                  45

Val Leu Phe Asp Lys Thr Ser Thr Arg Thr Arg Phe Ser Phe Asp Ala
50                  55                  60

Gly Ile Ala His Leu Gly Gly His Ala Ile Val Val Asp Ser Gly Ser
65                  70                  75                  80

Ser Gln Met Gly Lys Gly Glu Ser Leu Gln Asp Thr Ala Ala Val Leu
                85                  90                  95

Ser Arg Tyr Val Glu Ala Ile Val Trp Arg Thr Tyr Ala His Ser Asn
                100                 105                 110

Phe His Ala Met Ala Glu Thr Ser Thr Val Pro Leu Val Asn Ser Leu
                115                 120                 125

Ser Asp Asp Leu His Pro Cys Gln Ile Leu Ala Asp Leu Gln Thr Ile
                130                 135                 140

Val Glu Asn Leu Ser Pro Glu Glu Gly Pro Ala Gly Leu Lys Gly Lys
145                 150                 155                 160

Lys Ala Val Tyr Leu Gly Asp Gly Asp Asn Asn Met Ala Asn Ser Tyr
                165                 170                 175

Met Ile Gly Phe Ala Thr Ala Gly Met Asp Ile Ser Ile Ile Ala Pro
                180                 185                 190

Glu Gly Phe Gln Pro Arg Ala Glu Phe Val Glu Arg Ala Glu Lys Arg
```

```
            195                 200                 205
Gly Gln Glu Thr Gly Ala Lys Val Val Val Thr Asp Ser Leu Asp Glu
    210                 215                 220

Val Ala Gly Ala Asp Val Val Ile Thr Asp Thr Trp Val Ser Met Gly
225                 230                 235                 240

Met Glu Asn Asp Gly Ile Asp Arg Thr Thr Pro Phe Val Pro Tyr Gln
                245                 250                 255

Val Asn Asp Glu Val Met Ala Lys Ala Asn Asp Gly Ala Ile Phe Leu
            260                 265                 270

His Cys Leu Pro Ala Tyr Arg Gly Lys Glu Val Ala Ala Ser Val Ile
        275                 280                 285

Asp Gly Pro Ala Ser Lys Val Phe Asp Glu Ala Glu Asn Arg Leu His
    290                 295                 300

Ala Gln Lys Ala Leu Leu Val Trp Leu Leu Ala Asn Gln Pro Arg
305                 310                 315

<210> SEQ ID NO 21
<211> LENGTH: 533
<212> TYPE: PRT
<213> ORGANISM: Corynebacterium glutamicum

<400> SEQUENCE: 21

Met Ile Leu Gly Val Pro Ile Gln Tyr Leu Leu Tyr Ser Leu Trp Asn
1               5                   10                  15

Trp Ile Val Asp Thr Gly Phe Asp Val Ala Ile Ile Leu Val Leu Ala
            20                  25                  30

Phe Leu Ile Pro Arg Ile Gly Arg Leu Ala Met Arg Ile Lys Arg
        35                  40                  45

Arg Val Glu Ser Ala Ala Asp Ala Asp Thr Thr Lys Asn Gln Leu Ala
    50                  55                  60

Phe Ala Gly Val Gly Val Tyr Ile Ala Gln Ile Val Ala Phe Phe Met
65                  70                  75                  80

Leu Ala Val Ser Ala Met Gln Ala Phe Gly Phe Ser Leu Ala Gly Ala
                85                  90                  95

Ala Ile Pro Ala Thr Ile Ala Ser Ala Ala Ile Gly Leu Gly Ala Gln
            100                 105                 110

Ser Ile Val Ala Asp Phe Leu Ala Gly Phe Phe Ile Leu Thr Glu Lys
        115                 120                 125

Gln Phe Gly Val Gly Asp Trp Val Arg Phe Glu Gly Asn Gly Ile Val
    130                 135                 140

Val Glu Gly Thr Val Ile Glu Ile Thr Met Arg Ala Thr Lys Ile Arg
145                 150                 155                 160

Thr Ile Ala Gln Glu Thr Val Ile Pro Asn Ser Thr Ala Lys Val
                165                 170                 175

Cys Ile Asn Asn Ser Asn Asn Trp Ser Arg Ala Val Val Ile Pro
            180                 185                 190

Ile Pro Met Leu Gly Ser Glu Asn Ile Thr Asp Val Ile Ala Arg Ser
        195                 200                 205

Glu Ala Ala Thr Arg Arg Ala Leu Gly Gln Glu Lys Ile Ala Pro Glu
    210                 215                 220

Ile Leu Gly Glu Leu Asp Val His Pro Ala Thr Glu Val Thr Pro Pro
225                 230                 235                 240

Thr Val Val Gly Met Pro Trp Met Val Thr Met Arg Phe Leu Val Gln
                245                 250                 255
```

```
Val Thr Ala Gly Asn Gln Trp Leu Val Glu Arg Ala Ile Arg Thr Glu
            260                 265                 270

Ile Ile Ser Glu Phe Trp Glu Glu Tyr Gly Ser Ala Thr Thr Thr Ser
            275                 280                 285

Gly Thr Leu Ile Asp Ser Leu His Val Glu His Glu Glu Pro Lys Thr
            290                 295                 300

Ser Leu Ile Asp Ala Ser Pro Gln Ala Leu Lys Glu Pro Lys Pro Glu
305                 310                 315                 320

Ala Ala Ala Thr Val Ala Ser Leu Ala Ala Ser Ser Asn Asp Asp Ala
            325                 330                 335

Asp Asn Ala Asp Ala Ser Val Ile Asn Ala Gly Asn Pro Glu Lys Glu
            340                 345                 350

Leu Asp Ser Asp Val Leu Glu Gln Glu Leu Ser Ser Glu Glu Pro Glu
            355                 360                 365

Glu Thr Ala Lys Pro Asp His Ser Leu Arg Gly Phe Phe Arg Thr Asp
            370                 375                 380

Tyr Tyr Pro Asn Arg Trp Gln Lys Ile Leu Ser Phe Gly Gly Arg Val
385                 390                 395                 400

Arg Met Ser Thr Ser Leu Leu Leu Gly Ala Leu Leu Leu Ser Leu
            405                 410                 415

Phe Lys Val Met Thr Val Glu Pro Ser Glu Asn Trp Gln Asn Ser Ser
            420                 425                 430

Gly Trp Leu Ser Pro Ser Thr Ala Thr Ser Thr Ala Val Thr Thr Ser
            435                 440                 445

Glu Thr Ser Ala Pro Val Ser Thr Pro Ser Met Thr Val Pro Thr Thr
450                 455                 460

Val Glu Glu Thr Pro Thr Met Glu Ser Asn Val Glu Thr Gln Gln Glu
465                 470                 475                 480

Thr Ser Thr Pro Ala Thr Ala Thr Pro Gln Arg Ala Asp Thr Ile Glu
            485                 490                 495

Pro Thr Glu Glu Ala Thr Ser Gln Glu Glu Thr Thr Ala Ser Gln Thr
            500                 505                 510

Gln Ser Pro Ala Val Glu Ala Pro Thr Ala Val Gln Glu Thr Val Ala
            515                 520                 525

Pro Thr Ser Thr Pro
            530

<210> SEQ ID NO 22
<211> LENGTH: 711
<212> TYPE: PRT
<213> ORGANISM: Corynebacterium glutamicum

<400> SEQUENCE: 22

Met Lys Ser Met Asn Ile Ala Ala Ser Ser Glu Leu Val Ser Arg Leu
1               5                   10                  15

Ser Ser His Arg Arg Val Val Ala Leu Gly Asp Thr Asp Phe Thr Asp
            20                  25                  30

Val Ala Ala Val Val Ile Thr Ala Ala Asp Ser Arg Ser Gly Ile Leu
        35                  40                  45

Ala Leu Leu Lys Arg Thr Gly Phe His Leu Pro Val Phe Leu Tyr Ser
    50                  55                  60

Glu His Ala Val Glu Leu Pro Ala Gly Val Thr Ala Val Ile Asn Gly
65                  70                  75                  80

Asn Glu Gln Gln Trp Leu Glu Leu Glu Ser Ala Ala Cys Gln Tyr Glu
                85                  90                  95
```

-continued

Glu Asn Leu Leu Pro Pro Phe Tyr Asp Thr Leu Thr Gln Tyr Val Glu
            100                 105                 110

Met Gly Asn Ser Thr Phe Ala Cys Pro Gly His Gln His Gly Ala Phe
        115                 120                 125

Phe Lys Lys His Pro Ala Gly Arg His Phe Tyr Asp Phe Phe Gly Glu
    130                 135                 140

Asn Val Phe Arg Ala Asp Met Cys Asn Ala Asp Val Lys Leu Gly Asp
145                 150                 155                 160

Leu Leu Ile His Glu Gly Ser Ala Lys Asp Ala Gln Lys Phe Ala Ala
                165                 170                 175

Lys Val Phe His Ala Asp Lys Thr Tyr Phe Val Leu Asn Gly Thr Ser
            180                 185                 190

Ala Ala Asn Lys Val Val Thr Asn Ala Leu Leu Thr Arg Gly Asp Leu
        195                 200                 205

Val Leu Phe Asp Arg Asn Asn His Lys Ser Asn His His Gly Ala Leu
    210                 215                 220

Ile Gln Ala Gly Ala Thr Pro Val Tyr Leu Glu Ala Ser Arg Asn Pro
225                 230                 235                 240

Phe Gly Phe Ile Gly Gly Ile Asp Ala His Cys Phe Asn Glu Glu Tyr
                245                 250                 255

Leu Arg Gln Gln Ile Arg Asp Val Ala Pro Glu Lys Ala Asp Leu Pro
            260                 265                 270

Arg Pro Tyr Arg Leu Ala Ile Ile Gln Leu Gly Thr Tyr Asp Gly Thr
        275                 280                 285

Val Tyr Asn Ala Arg Gln Val Ile Asp Thr Val Gly His Leu Cys Asp
    290                 295                 300

Tyr Ile Leu Phe Asp Ser Ala Trp Val Gly Tyr Glu Gln Phe Ile Pro
305                 310                 315                 320

Met Met Ala Asp Ser Ser Pro Leu Leu Leu Glu Leu Asn Glu Asn Asp
                325                 330                 335

Pro Gly Ile Phe Val Thr Gln Ser Val His Lys Gln Gln Ala Gly Phe
            340                 345                 350

Ser Gln Thr Ser Gln Ile His Lys Lys Asp Asn His Ile Arg Gly Gln
        355                 360                 365

Ala Arg Phe Cys Pro His Lys Arg Leu Asn Asn Ala Phe Met Leu His
    370                 375                 380

Ala Ser Thr Ser Pro Phe Tyr Pro Leu Phe Ala Ala Leu Asp Val Asn
385                 390                 395                 400

Ala Lys Ile His Glu Gly Glu Ser Gly Arg Arg Leu Trp Ala Glu Cys
                405                 410                 415

Val Glu Ile Gly Ile Glu Ala Arg Lys Ala Ile Leu Ala Arg Cys Lys
            420                 425                 430

Leu Phe Arg Pro Phe Ile Pro Pro Val Val Asp Gly Lys Leu Trp Gln
        435                 440                 445

Asp Tyr Pro Thr Ser Val Leu Ala Ser Asp Arg Arg Phe Phe Ser Phe
    450                 455                 460

Glu Pro Gly Ala Lys Trp His Gly Phe Glu Gly Tyr Ala Ala Asp Gln
465                 470                 475                 480

Tyr Phe Val Asp Pro Cys Lys Leu Leu Leu Thr Thr Pro Gly Ile Asp
                485                 490                 495

Ala Glu Thr Gly Glu Tyr Ser Asp Phe Gly Val Pro Ala Thr Ile Leu
            500                 505                 510

```
Ala His Tyr Leu Arg Glu Asn Gly Ile Val Pro Glu Lys Cys Asp Leu
            515                 520                 525

Asn Ser Ile Leu Phe Leu Leu Thr Pro Ala Glu Ser His Glu Lys Leu
        530                 535                 540

Ala Gln Leu Val Ala Met Leu Ala Gln Phe Glu Gln His Ile Glu Asp
545                 550                 555                 560

Asp Ser Pro Leu Val Glu Val Leu Pro Ser Val Tyr Asn Lys Tyr Pro
                565                 570                 575

Val Arg Tyr Arg Asp Tyr Thr Leu Arg Gln Leu Cys Gln Glu Met His
                580                 585                 590

Asp Leu Tyr Val Ser Phe Asp Val Lys Asp Leu Gln Lys Ala Met Phe
            595                 600                 605

Arg Gln Gln Ser Phe Pro Ser Val Val Met Asn Pro Gln Asp Ala His
        610                 615                 620

Ser Ala Tyr Ile Arg Gly Asp Val Glu Leu Val Arg Ile Arg Asp Ala
625                 630                 635                 640

Glu Gly Arg Ile Ala Ala Glu Gly Ala Leu Pro Tyr Pro Pro Gly Val
                645                 650                 655

Leu Cys Val Val Pro Gly Glu Val Trp Gly Gly Ala Val Gln Arg Tyr
                660                 665                 670

Phe Leu Ala Leu Glu Glu Gly Val Asn Leu Leu Pro Gly Phe Ser Pro
            675                 680                 685

Glu Leu Gln Gly Val Tyr Ser Glu Thr Asp Ala Asp Gly Val Lys Arg
        690                 695                 700

Leu Tyr Gly Tyr Val Leu Lys
705                 710

<210> SEQ ID NO 23
<211> LENGTH: 357
<212> TYPE: PRT
<213> ORGANISM: Corynebacterium glutamicum

<400> SEQUENCE: 23

Met Ile Met His Asn Val Tyr Gly Val Thr Met Thr Ile Lys Val Ala
1               5                   10                  15

Ile Ala Gly Ala Ser Gly Tyr Ala Gly Gly Glu Ile Leu Arg Leu Leu
                20                  25                  30

Leu Gly His Pro Ala Tyr Ala Ser Gly Glu Leu Glu Ile Gly Ala Leu
            35                  40                  45

Thr Ala Ala Ser Thr Ala Gly Ser Thr Leu Gly Glu Leu Met Pro His
        50                  55                  60

Ile Pro Gln Leu Ala Asp Arg Val Ile Gln Asp Thr Ala Glu Thr
65                  70                  75              80

Leu Ala Gly His Asp Val Val Phe Leu Gly Leu Pro His Gly Phe Ser
                85                  90                  95

Ala Glu Ile Ala Leu Gln Leu Gly Pro Asp Val Thr Val Ile Asp Cys
                100                 105                 110

Ala Ala Asp Phe Arg Leu Gln Asn Ala Ala Asp Trp Glu Lys Phe Tyr
            115                 120                 125

Gly Ser Glu His Gln Gly Thr Trp Pro Tyr Gly Ile Pro Glu Met Pro
        130                 135                 140

Gly His Arg Glu Ala Leu Arg Gly Ala Lys Arg Val Ala Val Pro Gly
145                 150                 155                 160

Cys Phe Pro Thr Gly Ala Thr Leu Ala Leu Leu Pro Ala Val Gln Ala
                165                 170                 175
```

```
Gly Leu Ile Glu Pro Asp Val Ser Val Ser Ile Thr Gly Val Ser
            180                 185                 190
Gly Ala Gly Lys Lys Ala Ser Val Ala Leu Leu Gly Ser Glu Thr Met
        195                 200                 205
Gly Ser Leu Lys Ala Tyr Asn Thr Ser Gly Lys His Arg His Thr Pro
    210                 215                 220
Glu Ile Ala Gln Asn Leu Gly Glu Val Ser Asp Lys Pro Val Lys Val
225                 230                 235                 240
Ser Phe Thr Pro Val Leu Ala Pro Leu Pro Arg Gly Ile Leu Thr Thr
                245                 250                 255
Ala Thr Ala Pro Leu Lys Glu Gly Val Thr Ala Glu Gln Ala Arg Ala
            260                 265                 270
Val Tyr Glu Glu Phe Tyr Ala Gln Glu Thr Phe Val His Val Leu Pro
        275                 280                 285
Glu Gly Ala Gln Pro Gln Thr Gln Ala Val Leu Gly Ser Asn Met Cys
    290                 295                 300
His Val Gln Val Glu Ile Asp Glu Glu Ala Gly Lys Val Leu Val Thr
305                 310                 315                 320
Ser Ala Ile Asp Asn Leu Thr Lys Gly Thr Ala Gly Ala Ala Val Gln
                325                 330                 335
Cys Met Asn Leu Ser Val Gly Phe Asp Glu Ala Ala Gly Leu Pro Gln
            340                 345                 350
Val Gly Val Ala Pro
            355

<210> SEQ ID NO 24
<211> LENGTH: 388
<212> TYPE: PRT
<213> ORGANISM: Corynebacterium glutamicum

<400> SEQUENCE: 24

Met Ala Glu Lys Gly Ile Thr Ala Pro Lys Gly Phe Val Ala Ser Ala
1               5                   10                  15
Thr Thr Ala Gly Ile Lys Ala Ser Gly Asn Pro Asp Met Ala Leu Val
            20                  25                  30
Val Asn Gln Gly Pro Glu Phe Ser Ala Ala Val Phe Thr Arg Asn
        35                  40                  45
Arg Val Phe Ala Ala Pro Val Lys Val Ser Arg Glu Asn Val Ala Asp
    50                  55                  60
Gly Gln Ile Arg Ala Val Leu Tyr Asn Ala Gly Asn Ala Asn Ala Cys
65                  70                  75                  80
Asn Gly Leu Gln Gly Glu Lys Asp Ala Arg Glu Ser Val Ser His Leu
                85                  90                  95
Ala Gln Asn Leu Gly Leu Glu Asp Ser Asp Ile Gly Val Cys Ser Thr
            100                 105                 110
Gly Leu Ile Gly Glu Leu Leu Pro Met Asp Lys Leu Asn Ala Gly Ile
        115                 120                 125
Asp Gln Leu Thr Ala Glu Gly Ala Leu Gly Asp Asn Gly Ala Ala Ala
    130                 135                 140
Ala Lys Ala Ile Met Thr Thr Asp Thr Val Asp Lys Glu Thr Val Val
145                 150                 155                 160
Phe Ala Asp Gly Trp Thr Val Gly Gly Met Gly Lys Gly Val Gly Met
                165                 170                 175
Met Ala Pro Ser Leu Ala Thr Met Leu Val Cys Leu Thr Thr Asp Ala
```

```
                180             185             190
Ser Val Thr Gln Glu Met Ala Gln Ile Ala Leu Ala Asn Ala Thr Ala
            195             200             205
Val Thr Phe Asp Thr Leu Asp Ile Asp Gly Ser Thr Ser Thr Asn Asp
            210             215             220
Thr Val Phe Leu Leu Ala Ser Gly Ala Ser Gly Ile Thr Pro Thr Gln
225             230             235             240
Asp Glu Leu Asn Asp Ala Val Tyr Ala Ala Cys Ser Asp Ile Ala Ala
            245             250             255
Lys Leu Gln Ala Asp Ala Glu Gly Val Thr Lys Arg Val Ala Val Thr
            260             265             270
Val Val Gly Thr Thr Asn Asn Glu Gln Ala Ile Asn Ala Ala Arg Thr
            275             280             285
Val Ala Arg Asp Asn Leu Phe Lys Cys Ala Met Phe Gly Ser Asp Pro
            290             295             300
Asn Trp Gly Arg Val Leu Ala Ala Val Gly Met Ala Asp Ala Asp Met
305             310             315             320
Glu Pro Glu Lys Ile Ser Val Phe Phe Asn Gly Gln Ala Val Cys Leu
            325             330             335
Asp Ser Thr Gly Ala Pro Gly Ala Arg Glu Val Asp Leu Ser Gly Ala
            340             345             350
Asp Ile Asp Val Arg Ile Asp Leu Gly Thr Ser Gly Glu Gly Gln Ala
            355             360             365
Thr Val Arg Thr Thr Asp Leu Ser Phe Ser Tyr Val Glu Ile Asn Ser
            370             375             380
Ala Tyr Ser Ser
385

<210> SEQ ID NO 25
<211> LENGTH: 317
<212> TYPE: PRT
<213> ORGANISM: Corynebacterium glutamicum

<400> SEQUENCE: 25

Met Asn Asp Leu Ile Lys Asp Leu Gly Ser Glu Val Arg Ala Asn Val
1               5                   10                  15
Leu Ala Glu Ala Leu Pro Trp Leu Gln His Phe Arg Asp Lys Ile Val
            20                  25                  30
Val Val Lys Tyr Gly Gly Asn Ala Met Val Asp Asp Leu Lys Ala
            35              40                  45
Ala Phe Ala Ala Asp Met Val Phe Leu Arg Thr Val Gly Ala Lys Pro
50                  55                  60
Val Val Val His Gly Gly Pro Gln Ile Ser Glu Met Leu Asn Arg
65              70                  75              80
Val Gly Leu Gln Gly Glu Phe Lys Gly Phe Arg Val Thr Thr Pro
            85                  90                  95
Glu Val Met Asp Ile Val Arg Met Val Leu Phe Gly Gln Val Gly Arg
            100             105             110
Asp Leu Val Gly Leu Ile Asn Ser His Gly Pro Tyr Ala Val Gly Thr
            115             120             125
Ser Gly Glu Asp Ala Gly Leu Phe Thr Ala Gln Lys Arg Met Val Asn
            130             135             140
Ile Asp Gly Val Pro Thr Asp Ile Gly Leu Val Gly Asp Ile Ile Asn
145             150             155             160
```

```
Val Asp Ala Ser Ser Leu Met Asp Ile Ile Glu Ala Gly Arg Ile Pro
            165                 170                 175

Val Val Ser Thr Ile Ala Pro Gly Glu Asp Gly Gln Ile Tyr Asn Ile
        180                 185                 190

Asn Ala Asp Thr Ala Ala Gly Ala Leu Ala Ala Ile Gly Ala Glu
        195                 200                 205

Arg Leu Leu Val Leu Thr Asn Val Glu Gly Leu Tyr Thr Asp Trp Pro
    210                 215                 220

Asp Lys Ser Ser Leu Val Ser Lys Ile Lys Ala Thr Glu Leu Glu Ala
225                 230                 235                 240

Ile Leu Pro Gly Leu Asp Ser Gly Met Ile Pro Lys Met Glu Ser Cys
                245                 250                 255

Leu Asn Ala Val Arg Gly Gly Val Ser Ala Ala His Val Ile Asp Gly
            260                 265                 270

Arg Ile Ala His Ser Val Leu Leu Glu Leu Leu Thr Met Gly Gly Ile
        275                 280                 285

Gly Thr Met Val Leu Pro Asp Val Phe Asp Arg Glu Asn Tyr Pro Glu
    290                 295                 300

Gly Thr Val Phe Arg Lys Asp Lys Asp Gly Glu Leu
305                 310                 315

<210> SEQ ID NO 26
<211> LENGTH: 391
<212> TYPE: PRT
<213> ORGANISM: Corynebacterium glutamicum

<400> SEQUENCE: 26

Met Ser Thr Leu Glu Thr Trp Pro Gln Val Ile Ile Asn Thr Tyr Gly
1               5                   10                  15

Thr Pro Pro Val Glu Leu Val Ser Gly Lys Gly Ala Thr Val Thr Asp
                20                  25                  30

Asp Gln Gly Asn Val Tyr Ile Asp Leu Leu Ala Gly Ile Ala Val Asn
            35                  40                  45

Ala Leu Gly His Ala His Pro Ala Ile Ile Glu Ala Val Thr Asn Gln
        50                  55                  60

Ile Gly Gln Leu Gly His Val Ser Asn Leu Phe Ala Ser Arg Pro Val
65                  70                  75                  80

Val Glu Val Ala Glu Glu Leu Ile Lys Arg Phe Ser Leu Asp Asp Ala
                85                  90                  95

Thr Leu Ala Ala Gln Thr Arg Val Phe Phe Cys Asn Ser Gly Ala Glu
            100                 105                 110

Ala Asn Glu Ala Ala Phe Lys Ile Ala Arg Leu Thr Gly Arg Ser Arg
        115                 120                 125

Ile Leu Ala Ala Val His Gly Phe His Gly Arg Thr Met Gly Ser Leu
    130                 135                 140

Ala Leu Thr Gly Gln Pro Asp Lys Arg Glu Ala Phe Leu Pro Met Pro
145                 150                 155                 160

Ser Gly Val Glu Phe Tyr Pro Tyr Gly Asp Thr Asp Tyr Leu Arg Lys
                165                 170                 175

Met Val Glu Thr Asn Pro Thr Asp Val Ala Ala Ile Phe Leu Glu Pro
            180                 185                 190

Ile Gln Gly Glu Thr Gly Val Val Pro Ala Pro Glu Gly Phe Leu Lys
        195                 200                 205

Ala Val Arg Glu Leu Cys Asp Glu Tyr Gly Ile Leu Met Ile Thr Asp
    210                 215                 220
```

```
Glu Val Gln Thr Gly Val Gly Arg Thr Gly Asp Phe Phe Ala His Gln
225                 230                 235                 240

His Asp Gly Val Val Pro Asp Val Val Thr Met Ala Lys Gly Leu Gly
            245                 250                 255

Gly Gly Leu Pro Ile Gly Ala Cys Leu Ala Thr Gly Arg Ala Ala Glu
        260                 265                 270

Leu Met Thr Pro Gly Lys His Gly Thr Thr Phe Gly Gly Asn Pro Val
    275                 280                 285

Ala Cys Ala Ala Ala Lys Ala Val Leu Ser Val Val Asp Asp Ala Phe
290                 295                 300

Cys Ala Glu Val Ala Arg Lys Gly Glu Leu Phe Lys Glu Leu Leu Ala
305                 310                 315                 320

Lys Val Asp Gly Val Asp Val Arg Gly Arg Gly Leu Met Leu Gly
                325                 330                 335

Val Val Leu Glu Arg Asp Val Ala Lys Gln Ala Val Leu Asp Gly Phe
        340                 345                 350

Lys His Gly Val Ile Leu Asn Ala Pro Ala Asp Asn Ile Ile Arg Leu
        355                 360                 365

Thr Pro Pro Leu Val Ile Thr Asp Glu Glu Ile Ala Asp Ala Val Lys
    370                 375                 380

Ala Ile Ala Glu Thr Ile Ala
385                 390

<210> SEQ ID NO 27
<211> LENGTH: 538
<212> TYPE: PRT
<213> ORGANISM: Corynebacterium glutamicum

<400> SEQUENCE: 27

Met Ser Ser Thr Thr Ser Lys Thr Ser Glu Arg Gln Gln Pro Asp Ala
1               5                   10                  15

Pro Thr Ser Lys Leu Ser Lys Trp Ser Asp Lys Phe Leu Asn Gly Val
            20                  25                  30

Glu Thr Leu Gly Asn Lys Leu Pro Thr Pro Phe Thr Leu Phe Leu Ile
        35                  40                  45

Leu Phe Leu Ile Thr Ala Leu Ala Ser Ser Ile Met Ala Trp Met Asn
    50                  55                  60

Val Ser Val Ile Val Pro Gly Ser Asp Glu Glu Leu Phe Val Lys Gly
65                  70                  75                  80

Leu Phe Thr Gly Glu Gly Leu Thr Trp Leu Thr Thr Asn Leu Gly Ala
                85                  90                  95

Asn Tyr Ile Gly Phe Pro Pro Leu Leu Thr Val Leu Pro Ile Leu Leu
            100                 105                 110

Ala Val Gly Val Ala Glu Arg Ser Gly Met Leu Ala Ala Leu Ile Arg
        115                 120                 125

Lys Leu Phe Gly Ser Ala Lys Lys Ile Val Leu Pro Tyr Ala Val Gly
    130                 135                 140

Val Ile Gly Val Thr Ala Ser Ile Met Ala Asp Ala Ala Phe Val Val
145                 150                 155                 160

Val Pro Pro Leu Ala Ala Met Val Phe Lys Ala Ala Gly Arg His Pro
                165                 170                 175

Val Ala Gly Leu Leu Gly Ser Phe Ala Ala Val Gly Ala Gly Tyr Ser
            180                 185                 190

Thr Ala Ile Val Pro Thr Ser Leu Asp Ala Leu Phe Ala Gly Ile Thr
```

```
                195                 200                 205
Asn Ala Val Met Glu Thr Leu Pro Gly Ile Ala Thr Thr Glu Val Asn
210                 215                 220

Pro Val Ser Asn Tyr Tyr Phe Asn Ile Ala Ser Ser Ile Val Leu Gly
225                 230                 235                 240

Leu Leu Cys Gly Phe Leu Ile Asp Lys Val Leu Glu Pro Arg Met Trp
                245                 250                 255

Arg Gln Lys Ile Ala Thr Glu Tyr Ala Glu Ser Ile Glu Pro Thr Ser
                260                 265                 270

Ala Ala Asp Asp Glu Glu Ile Ser Ala Thr Leu Thr Ala Gln Glu Asn
                275                 280                 285

Arg Ala Leu Thr Ile Ser Met Trp Thr Thr Leu Ala Thr Ala Ile Ile
290                 295                 300

Val Leu Val Val Val Leu Ile Pro Gly Ser Pro Trp Arg Asn Glu Asp
305                 310                 315                 320

Gly Gly Phe Leu Pro Thr Ser Pro Leu Leu Ser Ser Val Val Phe Ile
                325                 330                 335

Val Phe Leu Phe Phe Met Val Met Gly Leu Ala Tyr Gly Met Val Val
                340                 345                 350

Gly Thr Ile Lys Asn Met Asp Asp Val Val Asn Met Met Gly Glu Ala
                355                 360                 365

Ile Lys Asp Met Ile Gly Phe Leu Val Leu Ala Phe Ile Leu Gly Gln
370                 375                 380

Phe Val Ala Leu Phe Asn Trp Thr Gly Ile Gly Thr Trp Thr Ala Val
385                 390                 395                 400

Gln Gly Ala Ala Gly Leu Glu Ala Ile Gly Leu Thr Gly Phe Pro Ala
                405                 410                 415

Ile Ile Ala Phe Ile Ile Leu Ala Ser Cys Leu Asn Leu Leu Ile Ile
                420                 425                 430

Ser Gly Ser Ala Met Trp Thr Leu Met Ala Ala Val Phe Val Pro Met
                435                 440                 445

Phe Ala Leu Leu Gly Tyr Glu Pro Ser Phe Ile Gln Ala Ala Phe Arg
450                 455                 460

Val Gly Asp Ser Ala Thr Gln Val Ile Thr Pro Leu Asn Pro Tyr Met
465                 470                 475                 480

Ile Val Ile Leu Gly Leu Leu Arg Arg Tyr Glu Pro Asp Ala Gly Leu
                485                 490                 495

Gly Thr Leu Met Ser Arg Leu Ile Pro Phe Val Ile Pro Phe Trp Leu
                500                 505                 510

Ala Trp Ala Thr Leu Leu Ala Ile Trp Phe Tyr Ala Asp Leu Pro Leu
                515                 520                 525

Gly Pro Gly Ser Ala Ile Phe Leu Glu Gly
                530                 535

<210> SEQ ID NO 28
<211> LENGTH: 102
<212> TYPE: PRT
<213> ORGANISM: Corynebacterium glutamicum

<400> SEQUENCE: 28

Met Trp Thr Leu Met Ala Ala Val Phe Val Pro Met Phe Ala Leu Leu
1               5                   10                  15

Gly Tyr Glu Pro Ser Phe Ile Gln Ala Ala Phe Arg Val Gly Asp Ser
                20                  25                  30
```

```
Ala Thr Gln Val Ile Thr Pro Leu Asn Pro Tyr Met Ile Val Ile Leu
        35                  40                  45

Gly Leu Leu Arg Arg Tyr Glu Pro Asp Ala Gly Leu Gly Thr Leu Met
 50                  55                  60

Ser Arg Leu Ile Pro Phe Val Ile Pro Phe Trp Leu Ala Trp Ala Thr
 65                  70                  75                  80

Leu Leu Ala Ile Trp Phe Tyr Ala Asp Leu Pro Leu Gly Pro Gly Ser
                 85                  90                  95

Ala Ile Phe Leu Glu Gly
            100
```

<210> SEQ ID NO 29
<211> LENGTH: 122
<212> TYPE: PRT
<213> ORGANISM: Corynebacterium glutamicum

<400> SEQUENCE: 29

```
Val Asp Glu Arg Ser Arg Phe Ala Arg Ser Val Phe Pro Asp Gly Glu
 1               5                  10                  15

Glu Pro Asp Pro Arg Phe Thr Leu Ala Asn Glu Arg Thr Phe Leu Ala
            20                  25                  30

Trp Thr Arg Thr Ser Leu Ala Phe Leu Ala Gly Gly Ile Ala Phe Glu
        35                  40                  45

Ala Phe Gln Ile Ser Gly Leu Ser Asp Thr Val Arg Thr Thr Ile Ala
 50                  55                  60

Val Phe Ile Ile Ala Val Gly Met Ile Ile Ala Ala Gly Ala Ala Val
 65                  70                  75                  80

Arg Trp Met Asn Val Glu Arg Ala Met Arg Lys Gln Lys Pro Leu Pro
                 85                  90                  95

Val Pro Ala Ile Ile Pro Phe Leu Ser Ile Ala Ala Leu Val Ala Ser
            100                 105                 110

Ala Ala Val Leu Val Leu Ile Ile Val Gln
        115                 120
```

<210> SEQ ID NO 30
<211> LENGTH: 105
<212> TYPE: PRT
<213> ORGANISM: Corynebacterium glutamicum

<400> SEQUENCE: 30

```
Met Arg Ile His Glu Asp Pro Gly Leu Gln Pro Glu Arg Thr Val Leu
 1               5                  10                  15

Ala Trp Asn Arg Thr Thr Val Ser Leu Ala Val Cys Ser Ala Ile Leu
            20                  25                  30

Leu Arg Trp Thr Asn Phe Tyr Gly Ile Phe Ala Leu Leu Pro Val Val
        35                  40                  45

Ile Leu Ser Gly Met Ala Ile Phe Ile Leu Phe Thr Gln Arg Val Arg
 50                  55                  60

Tyr Glu Arg Gln Ala Ile Gly Leu Ala Asp Asn Lys Leu Pro Pro Asn
 65                  70                  75                  80

Ile Val Gly Val Val Ser Leu Thr Val Thr Leu Leu Ala Phe Gly Ala
                 85                  90                  95

Ala Gly Ile Val Phe Val Phe Ile Asp
            100                 105
```

<210> SEQ ID NO 31
<211> LENGTH: 265

<212> TYPE: PRT
<213> ORGANISM: Corynebacterium glutamicum

<400> SEQUENCE: 31

```
Val Ala Gly Asp Lys Leu Trp Leu Cys Asp Val His Phe Pro Val Ala
1               5                   10                  15

Arg Cys Trp Glu Thr Thr Thr Gly Arg Tyr Leu Gly Gln Thr Leu Val
            20                  25                  30

Pro Ala Pro Leu Arg Asp Arg Ser Tyr Val Leu Glu Leu His Ser Asp
        35                  40                  45

Gln Gln Leu Gly Ala Val Ala Ala Ser Gly Lys Ser Gly Trp Ile Leu
    50                  55                  60

Thr Pro Gly Gln Ala Val Ala Thr Lys Ala Pro Asp Trp Thr Pro Pro
65                  70                  75                  80

Thr Arg Ala Thr Asp Leu Pro Gln Val Pro Ser Pro Trp Glu Ile Val
                85                  90                  95

Ala Val Arg Gly Gln Gly Leu Phe Glu Leu Gln Val Glu Thr Ser Arg
            100                 105                 110

Arg Thr Ala Leu Gly Arg Val Asn Ala Thr Gly Gly Val Asp Ile Gly
        115                 120                 125

Glu Leu Pro Pro Asn Gly Tyr Thr Ile Ser Ser Val Val Gln Ile Gly
    130                 135                 140

Asp Glu Tyr Ile Val Gly Arg Trp Val Glu Glu Tyr Arg Leu Asn Ser
145                 150                 155                 160

Lys Leu Glu Val Ile Ser Thr Lys Glu Leu Asp Ile Ser Ala Ser Gly
                165                 170                 175

Trp Lys Ser Lys Gly Thr Val Ala Tyr Leu Ser Glu Asp Thr His Ile
            180                 185                 190

Cys Phe Phe Asp Gln Val Ser Gly Ala Glu Leu Pro Ser Leu Gly Ile
        195                 200                 205

Ala Glu Gly His Gln Gly Glu Val Met Ser Ala Thr Ser Ser Glu Ser
    210                 215                 220

Ile Val Leu Ile Tyr Arg Arg Asn Pro Asn Asn Ser Met Ser Ile Val
225                 230                 235                 240

Pro Thr Ser Val Ala Thr Tyr Asp Asn Gly Thr Trp Thr Thr Met Pro
                245                 250                 255

Leu Gln Glu Ala Pro Ala Glu Leu Ser
            260                 265
```